(12) United States Patent
Marom et al.

(10) Patent No.: US 7,499,894 B2
(45) Date of Patent: Mar. 3, 2009

(54) CEREBRAL PROGRAMMING

(76) Inventors: Shimon Marom, 6 Ovadia Street, Haifa 34528 (IL); Goded Shahaf, 25 Tarshish Street, Arad 89066 (IL); Benny Rousso, 12 Henry Bergson Street, Rishon-Lezion 75801 (IL); Shlomo Ben Haim, 8 Efronl Street, Caesaria 38900 (IL)

( * ) Notice: Subject to any disclaimer, the term of this patent is extended or adjusted under 35 U.S.C. 154(b) by 763 days.

(21) Appl. No.: 10/662,987

(22) Filed: Sep. 15, 2003

(65) Prior Publication Data
US 2004/0131998 A1  Jul. 8, 2004

Related U.S. Application Data

(63) Continuation of application No. PCT/IL02/00204, filed on Mar. 13, 2002.

(60) Provisional application No. 60/337,846, filed on Nov. 8, 2001, provisional application No. 60/275,396, filed on Mar. 13, 2001.

(51) Int. Cl.
*G06N 5/00* (2006.01)
(52) U.S. Cl. .......................... 706/23; 706/45
(58) Field of Classification Search .................. 706/23; 89/1.13; 102/355
See application file for complete search history.

(56) References Cited

U.S. PATENT DOCUMENTS

| 5,215,086 A | 6/1993 | Terry, Jr. et al. |
| 5,231,988 A | 8/1993 | Wernicke et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,325,862 A | 7/1994 | Lewis et al. |
| 5,330,515 A | 7/1994 | Rutecki et al. |
| 5,335,657 A | 8/1994 | Terry, Jr. et al. |
| 5,396,896 A | 3/1995 | Tumey et al. |
| 5,522,863 A | 6/1996 | Spano et al. |
| 5,540,730 A | 7/1996 | Terry, Jr. et al. |
| 5,571,150 A | 11/1996 | Wernicke et al. |
| 5,648,636 A * | 7/1997 | Simpson et al. ............. 102/355 |
| 5,707,400 A | 1/1998 | Terry, Jr. et al. |
| 5,928,272 A | 7/1999 | Adkins et al. |
| 6,066,163 A | 5/2000 | John |

(Continued)

FOREIGN PATENT DOCUMENTS

WO   WO 93/01862   2/1993

(Continued)

OTHER PUBLICATIONS

Schultz, W.; "Predictive Reward Signal of Dopamine Neurons;" 1998; The American Physiological Society; pp. 1-27.

(Continued)

*Primary Examiner*—Wilbert L Starks, Jr.

(57) ABSTRACT

A method of training a biological neural network using a controller, comprising:
applying a cycle comprising:
stimulating a neural network by said controller applying at least an input signal to the network;
detecting an output response of the network by said controller; and
modifying said stimulation by said controller for at least a period of time if said response matches a desired at least approximate response; and
repeating said cycle of stimulation, detection and modification at least one more time until said neural network is trained to generate a desired output response for said input signal.

66 Claims, 12 Drawing Sheets

U.S. PATENT DOCUMENTS

| | | | |
|---|---|---|---|
| 6,104,956 | A | 8/2000 | Naritoku et al. |
| 6,171,239 | B1 | 1/2001 | Humphrey |
| 6,341,236 | B1 | 1/2002 | Osorio et al. |
| 6,843,158 | B2 * | 1/2005 | Garcia et al. ............ 89/1.13 |
| 2002/0002390 | A1 | 1/2002 | Fischell et al. |

FOREIGN PATENT DOCUMENTS

| | | |
|---|---|---|
| WO | WO 93/02744 | 2/1993 |
| WO | WO 97/45160 | 12/1997 |
| WO | WO 98/06342 | 2/1998 |
| WO | WO 00/74777 | 12/2000 |
| WO | WO 01/47463 | 7/2001 |

OTHER PUBLICATIONS

Gisiger, T. et al.; "Computational Models of Association Cortex;" 2000; Current Opinion in Neurobiology; vol. 10; pp. 250-259.

Wessberg, J. et al.; Real-Time Prediction of Hand Trajectory by Ensembles of Cortical Neurons in Primates; Nov. 16, 2000; Nature; vol. 408; pp. 361-365.

Buonomano, D. V. et al.; "Cortical Plasticity: From Synapses to Maps;" 1998; Annu. Rev. Neurosci.; vol. 21; pp. 149-186.

"Definition of Learning" from "Web Dictionary of Cybernetics and Systems" downloaded <http://pespmcl.vub.ac.be/ASC/LEARNING.html> on Mar. 15, 2005.

Shahaf, G. et al.; "Learning in Networks of Cortical Neurons"; Nov. 15, 2001; The Journal of Neuroscience; vol. 21(22); pp. 8782-8788.

Chapin, J. K. et al.; "Real-Time Control of a Robot Arm Using Simultaneously Recorded Neurons in the Motor Cortex;" Jul. 1999; Nature Neuroscience; vol. 2; No. 7; pp. 664-670; 1999 Nature America Inc.; <http://neurosci.nature.com>.

* cited by examiner 1 msec

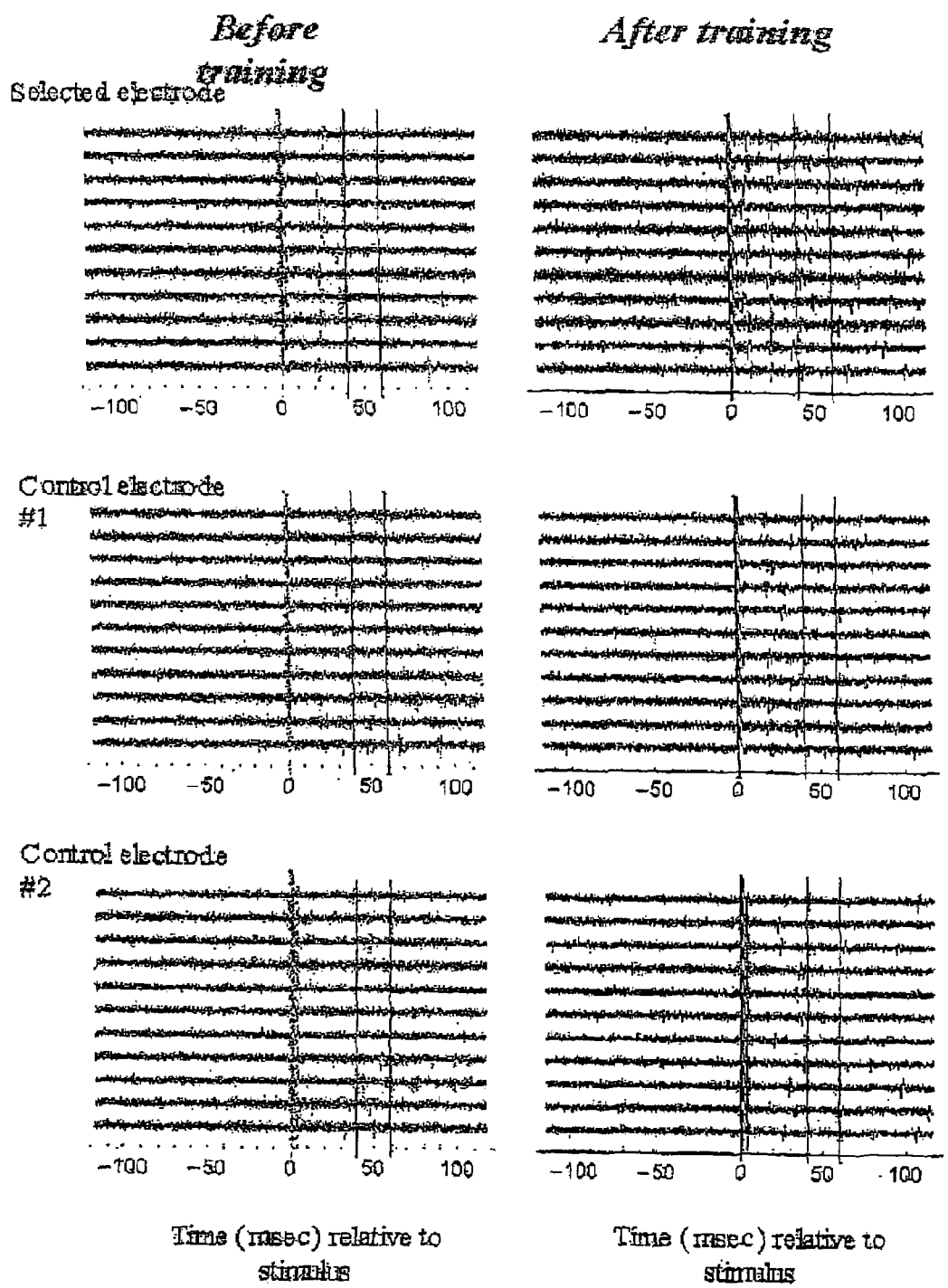

US 7,499,894 B2

CEREBRAL PROGRAMMING

RELATED APPLICATIONS

The present application is a continuation of PCT Application No. PCT/IL02/00204 filed on Mar. 13, 2002. This application also claims the benefit under 35 U.S.C. §119(e) of U.S. Provisional Application No. 60/337,846, filed on Nov. 8, 2001 and U.S. Provisional Application No. 60/275,396, filed on Mar. 13, 2001. All the disclosures of the above listed applications are incorporated herein by reference.

FIELD OF THE INVENTION

The present invention relates to methods of interacting with and/or affecting biological neural networks, for example, in-vivo and in-vitro networks.

BACKGROUND OF THE INVENTION

The brains of animals are formed of neurons interconnected into neural networks. A particular property of these neural networks is that they can be trained to have appropriate responses to various stimuli. In recent years, neurons are being cultivated outside the body and there is some desire to build computers based on or aided by biological neural networks, rather than on sequential electronic logic or artificial neural networks.

To date, however, no significant controlled training of neurons has been achieved. "Natural" in-vivo training of neurons, for example, teaching people to play the piano, has been achieved, of course. In some experiments, the stimulation signals are provided directly to neurons in the brain, rather than to sensory neurons. However, even such training does not allow any artificial control of the training process. What has been achieved artificially is causing two neurons to be synchronized in their behavior, by stimulating both the neurons simultaneously, several times.

The current theory for explaining neural learning, for example described in Schultz W., "Predictive Reward Signal of Dopamine Neurons", in J. Neurophysiol. 80:1-27 (1998), Schultz W and Dickinson A, "Neural Coding of prediction Errors", in Annu. Rev. Neurosci. 23:473-500 (2000), Spangel R and Weiss F, "The dopamine Hypothesis of Reward: Past and Current Status:, in Trends Neurosci, 22:521-527 (1999), Gisiger T, Dehaen S and Changeux J P, "Computational Models of Associative Cortex", Curr Opin Neurobiol, 10:250-259 (2000) and Kalivas P W and Nakamura M, "Neural Systems for Behavioral Activation and Reward", Curr Opin Neurobiol, 9:223-227 (1999), the disclosures of which are incorporated herein by reference, postulate a rewarding "circuit" that generates a signal that acts as a reward when a salient event occurs or a goal is achieved, which signal causes the neural network to retain or change the last applied response, as the proper, learned response to an input stimulus.

Other theories have been proposed for learning on a behavioral level. For example, C. Hull, "Principles of Behavior" Appleton-Century-Crofts, New-York (1943) and E. R. Guthrie, "Psychological Facts and Psychological Theory", in Psychological Bulletin 43 (1946) [Presidential address of the APA, Evanston, Ill. (1945)], the disclosures of which are incorporated herein by reference, suggest that when a goal is achieved, a resulting reward acts to reduce the driving stimuli of the learning process. There is no clear mechanism connecting cognitive theories and neuronal theories of learning or activity.

The functional structure of the brain includes multiple functional areas, some of which (e.g., the motor and sensory portions) are arranged in a generally hierarchical manner, in that a higher level area uses input from a lower level area or sends commands to a lower level area. A general mapping of brain areas to key functions is known. In addition, various methods of stimulating living brains and detecting activity in the brain are known as well.

J Wessberg, C R Stambaugh, J D Kralik, P D Beck, M Laubach, J K Chapin, J Kim, S J Biggs M A Srinivasan and M A L Nicolelis, "Real-Time Prediction of hand Trajectory by Ensembles of cortical Neurons in Primates" in Nature 408: 6810 (2000) p 361, the disclosure of which is incorporated herein by reference, is exemplary of several attempts to interface actuators to living neural networks. In this paper, an animal is trained to control a robotic arm using its brain's motor center, via electrodes attached to areas in the motor center associated with the desired movement. This paper also suggests using an electrode array applied to a brain, to detect activation patterns that correspond to various actions. Thus, the brain can effect an action, for example using a prosthetic attachment, when the brain "thinks" the patterns, and the patterns are detected by the electrode array.

D V Buonomano and M M Merzenich in "Cortical Plasticity: From Synapses to Maps", Annu. Rev. Neurosci. 21:149-186 (1998), the disclosure of which is incorporated herein by reference, describes various experiments performed to study learning in the brain. In particular, on page 160 an experiment showing in-vivo pairing of vision neurons with external stimuli is described. The correlation between the activity of these neurons and the occurrence of an event in the visual field was modified, by stimulating the neurons electrically when the event occurs.

This paper also discusses the plasticity of the cortex, for example, in receiving inputs from local or remote areas and in changing the function and/or location of a function, in response to training.

Learning by humans, and animals as far as is known, is generally achieved through the use of motivation. In a typical learning situation, an animal or human is rewarded for good results and/or punished for bad results. The reward may have various forms, including immediate reward and punishment, and, in humans, delayed reward and punishment, which, however, is converted into an immediate reward or punishment by the actions of the human consciousness.

One difficulty in training animals comes from the lack of a delayed reward/punishment mechanism. Another difficulty is that it is difficult, if not impossible, to provide an animal with exact feedback and/or pointers to what exact item it did not learn right, so that training can focus on those items. With a human, both of these are possible, albeit, sometimes frustrating.

Various neural stimulators are known in the art, for example, U.S. Pat. Nos. 6,341,236, 6,066,163 and 5,522,863 and US patent application publication US 2002/002390 A1, the disclosures of which are incorporated herein by reference. Various circuitry, software and other components and/or parameter settings described in these patents may find use in some embodiments of the present invention, for example as set out below.

SUMMARY OF THE INVENTION

An aspect of some embodiments of the invention relates to a method of training a neural network to provide a desired output in response to a given input. In an exemplary embodiment of the invention, the training method includes stimulating a neural network until a desired output signal is generated, and then stopping, or otherwise changing the stimulation, for a rest period so that the connection pattern in the network that generated the desired output, will become established. It has been found that the desired output signal, or an approximation thereof will be typically generated after a sufficient number of trials, in a significant percentage of the networks. This generation is then reinforced by the rest period.

In an exemplary embodiment of the invention, the training is closed loop in that the decision of when and how long to provide a rest period is predicated on the behavior of the network.

It should be noted that in some embodiments of the invention the enforced "rest period" is used for purposely actively controlling (e.g., changing) the learning behavior of the neurons, as opposed to "standard" methods in which the neurons are allowed and expected to act in their normal fashion. Other types of such control are described below, for example, enforcing a "busy" period, to interfere with learning. Optionally, a machine is used to apply the stimulation and determine the responses to the network behavior.

In an exemplary embodiment of the invention, the stimulation and rest cycle is repeated, possibly updating the desired output signal, to further refinements. The network may be stimulated at one or more randomly selected points. Alternatively, points that provide a suitability indication, for example, generating a first approximation to the desired output signal when stimulated, are used.

In an exemplary embodiment of the invention, the stimulation signal is the input signal. Alternatively, two stimulation (or more) signals are provided, the input signal, which may or may not be stopped during the rest period and a general stimulation signal, whose purpose may be, for example, to increase the number of neuronal connections that are open to change. Thus, in accordance with one possible explanation, when the stimulation is stopped, the number of connections open to change will decrease, establishing the new input-output pattern.

In an exemplary embodiment of the invention, the neural network is outside the body, for example being cultured on a substrate. Alternatively, the neural network is inside the body, for example, being a part of a central-, a peripheral- or a sensory- or a motor- or autonomic-nervous system of a human or other animal. In some embodiments of the invention, direct stimulation and/or readout of neurons is practiced. In other embodiments, interaction with neurons is via natural input and output neuronal pathways, such as the senses and body reactions.

In an exemplary embodiment of the invention, a training-affecting pharmaceutical for in-vivo use is evaluated by testing the effect of the pharmaceutical on the learning ability of an in-vivo or in-vitro neural network. In an exemplary embodiment of the invention, a plurality of neural networks are trained using a same protocol, except that some of the networks are treated with the pharmaceutical. The effects of the pharmaceutical (or other treatment or environmental condition) are evaluated, for example, by comparing time to learn, learning success rate and/or retention time.

An aspect of some embodiments of the invention relates to imposing a teaching on a brain by artificially controlling the learning process, optionally, in a manner that bypasses conscious involvement in, or control of, learning and/or which bypasses motivation-based mechanisms of learning. In an exemplary embodiment of the invention, the teaching is imposed by pairing the activation of two previously unsynchronized neurons, optionally using feedback. Alternatively or additionally, the teaching is imposed by imposing a new spatial and/or temporal activity pattern on a part of the brain.

Optionally, the training is applied while a person is asleep. Possibly, but not necessarily, the training uses non-invasive stimulation and/or monitoring of brain areas. Optionally, a person's reporting ability is utilized in controlling the teaching process, for example, to assist in determining when a desired output is achieved by the brain. Thus, while the person's consciousness is assisting in the learning process it is doing so in a manner unlike a normal learning process and possibly without being used to provide immediate or delayed motivation. In an exemplary embodiment of the invention, an external device is used to provide one or more "normal" learning functions that are typically provided by the person himself, for example, that of providing feedback to the neurons of the brain whether the training was achieved.

In an exemplary embodiment of the invention, the imposed teaching generates complex behavior, for example, including multiple modalities, sustained activity and/or a noticeable behavioral effect.

In an exemplary embodiment of the invention, the teaching is imposed by selectively destabilizing and/or stabilizing connections between neurons in a neural network, so that the stabilized connections produce a desired response from the neural network. Optionally, the extinction or reduction of an undesired behavioral response or perception is achieved by destabilization of an undesired network response. Possibly, the destabilization is by applying a stimulation signal or presenting a stimulating environment (e.g., a movie). Alternatively or additionally, the stabilization is by reducing a stimulation level, for example stopping (or reducing) a stimulating signal or stimulating environment, or using a suitable pharmaceutical such as a slow or fast acting sedative.

In an exemplary embodiment of the invention, the stimulating signal is spatially restricted, for example, to a part of the brain in which destabilization is desired, for example, using magnetic stimulation. Alternatively, non-specific stimulation may be practiced. Alternatively or additionally, the stimulating signal is functionally restricted to neurons that are already interconnected, for example by using the input signal as the stimulation signal.

In an exemplary embodiment of the invention, the training is applied to motor regions, for enabling or enhancing control of prosthetic devices. In one example, the training is used to "teach" the brain a correspondence function between electronic feedback from a prosthetic limb and the actuation of the limb by the brain. This actuation may be natural, for example using nerve axons to the muscle or to a transducer at the limb. Alternatively, the commands of the motor region are read, for example, using an electrode array, or a bundle of electrodes, and forwarded electronically to the limb. In an exemplary embodiment of the invention, a person is trained in the control of an artificial limb by a process in which a part of the motor region is repeatedly stimulated until a desired response is achieved by the limb, and then the stimulation is stopped. The stimulation may, in some cases, be directed to areas (or match patterns) which are known to control the, or involved with, various motor actions.

Alternatively to controlling artificial limbs, a same protocol may be used to teach a person new motor programs, for example, a new hand motion.

In an exemplary embodiment of the invention, when teaching large volumes of subject matter, the brain is trained to perform a small number (or even one) example, for example a particular hand motion. The trainee is then instructed to perform various exercises (e.g., a series of hand motions similar to the particular one) that enable the brain to extrapolate and vary the imposed motion, to a range.

In an exemplary embodiment of the invention, an imposed pattern, for example a particular hand motion, is created floating (e.g., unconnected to any known situation) and the user is exercised (e.g., to perform various motor activities that may inadvertently activate the floating pattern) in order to find the pattern. Once "found", various training methods (e.g., standard or using the methods described herein) may be used to link the already known motion to a stimulus, such as a command or a visual stimulus. Conversely, the methods described herein may be used to link a pattern that was learned using "standard" methods, to a given stimulus. Thus, in an exemplary embodiment of the invention, standard and novel training methods are combined, by replacing one or more elements (or steps) of one, with the other. In some cases, the order of learning is changed from that of standard methods (e.g., learning the linkage before learning the steps that are linked).

In an exemplary embodiment of the invention, training the brain is used to enhance and/or support the use of direct neural-electrical interfaces. In an exemplary embodiment of the invention, the imposed pattern is used to convert between a diffuse activation pattern (as typical in the brain) and a localized pattern (which is typically easier to read and/or write using interface element).

In one exemplary application, the training is used to "define" areas in the brain that serve as input areas, for example by training the brain to respond to various patterns imposed on the input areas, in predetermined action areas. Then, input to the brain can be provided via the input areas, which input causes stimulation in the action areas. The brain then learns to associate stimulation in the action areas with various inputs. It is noted that the input areas may be quite large, rather than being single neurons. Alternatively or additionally, the action areas are areas having known activity. Such training may be applied before and/or after the interface is connected and may, in some cases, be applied by the interface itself.

In another exemplary embodiment, the brain is trained to transform various action patterns into activation of designated output areas. For example, the training can map a neural activation pattern that arises when thinking of a movement, into stimulation of two particular output areas. These output areas can typically be more simply read than reading a complete, diffuse, activation pattern typically found in the brain, especially when using low cost and/or small devices and/or in noisy conditions. Alternatively or additionally, user directed activation of the output area may follow the trained activation, allowing the output of signals not related to any taught pattern.

In an exemplary embodiment of the invention, such an I/O area is used to allow the brain to interface with various devices controlled by the brain and/or to support interfacing between different parts of the brain.

An aspect of some embodiments of the invention relates to modifying the statistics of connections in the brain, to effect general changes in the pattern of activation propagation in the brain. In some embodiments of the invention, the modification does not substantially affect the external functioning of the brain (e.g., conversion of input to output). Alternatively, the modification does affect the functioning of the brain. Optionally, the changes are used to support input/output operations between the brain and a brain interface.

In one exemplary application, the above training method is used to prevent certain pathways (e.g., chains of neurons or chains of groups of neurons) of connection between two areas of the brain. In an exemplary embodiment of the invention, such prevention is achieved by interfering with the synchronization of neurons that are along the pathway and/or by imposing a new pattern that disrupts the pathway. By allowing a sufficient number of alternative pathways, the functioning of the brain may remain substantially unaffected. However, reading out the brain using sensors may be simplified due to the more orderly paths of signals in the brain. Alternatively or additionally, susceptibility to epilepsy is reduced, ability to control epilepsy is increased and/or undesirable interaction between different brain parts is reduced.

In another exemplary embodiment, the above training method is used to strengthen or create connections between two brain areas, for example, to assist in overcoming congenial, organic, trauma or other damage to the brain, or to provide new capabilities by interconnecting two previously unconnected brain areas.

In another exemplary embodiment, training is used to link two parts of the brain together, for example, a vibration sensory input to an auditory processing center. This type of chaining may be useful, for example, for teaching the use of a prosthetic hearing aid.

In an exemplary embodiment of the invention, the linking of brain areas and/or other modifications are enhanced by adding artificial conducing pathways in the brain, for example wires and/or amplifiers. Alternatively or additionally, one long-term effect of the training is the creating of new axons or other neural tissue that interconnect different areas, possibly in addition to new pathways created by rearrangement of synapses. Once such natural connections are created, the artificial means may be phased out, dissolve on their own and/or removed.

In another exemplary embodiment of the invention, a new functional brain area is created, by training an existing brain area to process input and generate output in a certain manner. In an exemplary embodiment of the invention, logic circuits (e.g., "NAND"), memory circuits, amplification circuits and/or pattern matching circuits are created in the brain. In one example, the new brain area processes input and generates output, for example retrieving memories from a look-up-table, performing calculations or imposing behavioral restraints on an animal. In another example, the new brain area controls the flow of activation, for example, by preventing activation from propagating along undesired pathways. This control of flow activation may be used to prevent epileptic fits, by detecting an ectopic activation and blocking its pathways. In another example, such selective allowance of flow of information is used to urge certain parts of the brain to participate in an activity, e.g., by forcefully simulating them.

In another exemplary embodiment of the invention, the new brain function is used to enhance (e.g., make trainable, more easily trainable and/or conscious) control and/or reporting of bodily functions, for example, body functions that are detected and/or controlled via vagus nerves and intra-brain sensing cells.

An aspect of some embodiments of the invention relates to apparatus for training a living neural network, comprising a sensor for sensing an output of the network, a stimulator for generating an input to the network and an optional second stimulator for controlling the network's learning behavior. A controller synchronizes the activity of the various components and applies a desired training regime. In an exemplary embodiment of the invention, the apparatus is laboratory based and used to impose a training that will prevent, counteract, confine or reduce epilepsy attacks. Alternatively or additionally, the apparatus is used to lessen or modify a sensation of pain. In an alternative embodiment of the invention, the device is mobile and may be used for periodic training and/or for applying a training sequence when an uncontrolled event (e.g., pain, epilepsy attack), occurs. Optionally, the device is implanted, partly or wholly and may be programmed and/or debriefed using wireless means, for example as known in the art of cardiac pacemakers.

An aspect of some embodiments of the invention relates to a device that is programmed and/or designed to utilize a "trained" neural network. In an exemplary embodiment of the invention, the device uses the previous training to assist an I/O interaction with a person or animal. Alternatively or additionally, the device uses the training to impose a certain behavior (e.g., a bark in the case of a dog), on the person or animal. Alternatively or additionally, the device provides a missing (or new) function for the neural network, for example, being an interface to a GPS system, a laptop computer or a cellular telephone.

In an exemplary embodiment of the invention, a living animal sensor is provided, with an animal providing the sensing (e.g., sense of smell, hearing) and the device processing the sensing and/or applying context dependent computation to determine and/or impose a course of action. In one example, a seeing-eye dog may be used as a smoke sensor. However, when smoke is detected, not only will the dog bark (as usually), but the device (e.g., implanted or worn) will generate an alarm transmission to an emergency service.

An aspect of some embodiments of the invention relates to learning based drug screening. In an exemplary embodiment of the invention, an in-vivo or in-vitro neural network is trained under the influence of drugs, or without, to determine the effect of the drugs on the ability and/or other parameters of learning. This may be used to detect undesirable psychoactive side effects and/or to assist in developing brain-enhancing drugs. In an exemplary embodiment of the invention, if a rate of learning in a mouse goes down when a drug is administered, a negative side effect is suspected. It should be noted that the rate of learning, as well as other parameters, such as duration of retention, may be measured directly form the network, thereby reducing various types of inference. Alternatively or additionally, by training in a way which bypasses motivation, higher resolution, shorter times and/or better less interference with the learning process itself may be achieved. The nature of the training method may also allow a same animal to be tested with various drugs and/or dosages. Erasure of learning may also be used for such within-animal testing.

Similarly, in an exemplary embodiment of the invention, such training and testing is used to diagnoses and/or monitor various psycho-degenerative diseases and/or their treatments. Optionally, such training is used to assess in real-time—e.g., a few minutes or an hour, and/or non-invasively, a degree of nutrient flow to a brain area. This may assist in diagnosing and treating strokes and/or chronic blood flow problems to the brain and/or other neuronal tissue.

There is thus provided in accordance with an exemplary embodiment of the invention, a method of training a biological neural network using a controller, comprising:

applying a cycle comprising:
stimulating a neural network by said controller applying at least an input signal to the network;
detecting an output response of the network by said controller; and
modifying said stimulation by said controller for at least a period of time if said response matches a desired at least approximate response; and repeating said cycle of stimulation, detection and modification at least one more time until said neural network is trained to generate a desired output response for said input signal.

Optionally, said input signal is a localized signal and wherein stimulating comprises applying a less localized stimulation. Optionally, said modifying comprises reducing said less localized stimulation. Alternatively or additionally, said modifying comprises increasing said less localized stimulation.

In an exemplary embodiment of the invention, said input signal is a specific signal and wherein stimulating comprises applying a less specific stimulation.

In an exemplary embodiment of the invention, said modifying comprises modifying said input signal.

In an exemplary embodiment of the invention, said modifying comprises stopping said stimulation.

In an exemplary embodiment of the invention, said modifying is applied in a manner known to affect a stability of connections in said network. Alternatively or additionally, said modifying is applied in a manner known to affect a learning behavior of said neurons of said network.

In an exemplary embodiment of the invention, said stimulating comprises stimulating using a magnetic field stimulator. Alternatively or additionally, said stimulating comprises stimulating using an electric current.

In an exemplary embodiment of the invention, said modifying comprises applying a chemical agent. Alternatively or additionally, said modifying comprises applying an electric field.

In an exemplary embodiment of the invention, the method comprises modifying said method by said controller in response to a response of said network to said method.

In an exemplary embodiment of the invention, said desired output response is a particular defined response. Alternatively, said desired output response is a random response pattern indicative of an unlearning by said network.

In an exemplary embodiment of the invention, said desired output response is a spatial shift in a portion of said network that responses to said input, from a previous responding portion to a shifted responding portion.

In an exemplary embodiment of the invention, the method comprises changing said input pattern during a repetition cycle. Alternatively or additionally, the method comprises increasing a resolution of said input pattern between repetition cycles. Alternatively or additionally, the method comprises requiring an output response with a reduced range of acceptable values in subsequent repetition cycles.

In an exemplary embodiment of the invention, repeating comprises repeating until an area of said network is organized to act as an input interface for said network for direct setting of network values not via a network's standard inputs. Alternatively or additionally, repeating comprises repeating until an area of said network is organized to act as an output interface for said network for direct receiving of network values not via a network's standard outputs.

In an exemplary embodiment of the invention, the method comprises:
providing a complex output response pattern to inputs to be trained into said network;
dividing said response pattern into sub-patterns;
training said sub-patterns individually; and
linking said sub-patterns.

In an exemplary embodiment of the invention, the method comprises training a desired output response pattern to inputs as a whole into said network.

In an exemplary embodiment of the invention, said network is an in-vitro network. Optionally, said network is grown in a container. Alternatively, said network is excised from a living body to a container.

In an exemplary embodiment of the invention, the method comprises:

providing a potential environmental contaminant;

repeating said method under at least two conditions of said contaminant; and comparing a response of said network to said method to determine an effect of said contaminant on training of said network.

In an exemplary embodiment of the invention, said network is an in-vivo network in a living non-human animal. Optionally, the method comprises:

providing a potential environmental contaminant;

repeating said method under at least two conditions of said contaminant; and comparing a response of said network to said method to determine an effect of said contaminant on training of said animal. Alternatively or additionally, the method comprises:

selecting a network portion of said animal that is coupled to a sensing ability of said animal; and training said network portion to output at least an indication of a sensing by said animal.

In an exemplary embodiment of the invention, said input is a command that can be sensed by said animal and wherein said desired output is a behavioral response of said animal. Optionally, said input and said output are inter-related using a complex logic, including at least two logic steps.

In an exemplary embodiment of the invention, said network is an in-vivo network in a living human. Optionally, said network is a GI motor complex. Alternatively, said network is a nervous plexus. Alternatively, said network is comprised in a brain.

In an exemplary embodiment of the invention, said controller replaces at least one natural learning related function of said brain. Optionally, said output is measured on said brain. Alternatively or additionally, said output is measured as a response of said human. Alternatively or additionally, said input is provided directly to said brain. Alternatively or additionally, said stimulation is provided directly to said brain. Alternatively or additionally, said stimulation is provided to said brain via natural senses. Alternatively or additionally, said input is provided to said brain via natural senses.

In an exemplary embodiment of the invention, modifying said stimulation comprising controlling the propagation of a signal inside said brain. Alternatively or additionally, said method is used to rehabilitate an old function of said network. Alternatively or additionally, said method is used to teach a new function to said network. Alternatively or additionally, said method is used to teach new motor programs to said network. Alternatively or additionally, said method is used to create a new pathway in said brain. Alternatively or additionally, said method is used to create a new function area in said brain. Alternatively or additionally, said method is used to remap a function from one brain area to another in said brain. Alternatively or additionally, said method is used to erase a learned pattern from said brain. Alternatively or additionally, said method is used to create a digital logic functioning area in said brain. Alternatively or additionally, said method is used to train the brain in the use of an artificial organ. Optionally, said organ is a replacement organ. Alternatively, said organ is a new organ not corresponding to a previous organ controlled by said brain.

In an exemplary embodiment of the invention, said human is not conscious during the application of said method. Alternatively or additionally, said human is not in control of learning processes imposed by said method.

In an exemplary embodiment of the invention, the method comprises not motivating said human in response to the output.

Optionally, said human reports said output. Alternatively or additionally, said human generates said input.

In an exemplary embodiment of the invention, the method comprises performing actions by said human to capture previously trained un-associated input-output response patterns.

In an exemplary embodiment of the invention, said input is an input internal to said brain. Alternatively or additionally, said output is an output internal to said brain. In an exemplary embodiment of the invention, said output comprises controlling an epilepsy attack.

In an exemplary embodiment of the invention, said output comprises reducing a sensation of pain.

There is also provided in accordance with an exemplary embodiment of the invention, an animal trained as described herein.

There is also provided in accordance with an exemplary embodiment of the invention, apparatus for training an in-vivo neural network, comprising:

an input stimulator that generates an input stimulation to said network;

a detector that detects at least an indication of a response of said network; and a controller that selectively controls said input stimulator such that if a desired output is detected, said input stimulation is changed.

Optionally, at least one of said simulator and said detector is implanted in vivo. Alternatively, said apparatus is external to a body on which it is used.

In an exemplary embodiment of the invention, said apparatus is mobile with a body on which it is used.

In an exemplary embodiment of the invention, the apparatus comprises an optional general stimulator that is operative to stimulate an area of the network larger than that used for receiving said input stimulation.

Optionally, said general stimulator comprises a TMS (trans-carnial magnetic stimulator). Alternatively or additionally, said detector detects a signal generated in said network. Alternatively or additionally, said detector detects a signal off of an object controlled by said network.

Optionally, said detector comprises an EMG sensor. Alternatively or additionally, said detector comprises an EEG sensor. Alternatively or additionally, said detector comprises an neural electrode.

In an exemplary embodiment of the invention, said stimulator directly stimulates said network via neural tissue which is trained by said apparatus. Alternatively, said stimulator indirectly stimulates said network through neural tissue which is not trained by said apparatus.

In an exemplary embodiment of the invention, said controller is programmed to training said network in a particular manner. Alternatively or additionally, said controller is programmed to maintain a training of said network.

There are also provided in accordance with an exemplary embodiment of the invention, apparatus for interfacing with an in-vivo neural network, that has been trained to include an unnatural input or output area in which a signal generated by the network is more easily detected or a signal input to the network will interact with similar functioning and inter-related neurons, comprising:

at least one of an neuronal input and a neuronal output;

a payload apparatus to be interfaced with said network; and a controller that interfaces said payload and said network, by translating a signal from said trained area or to said area as being directed to said trained input or output. Optionally, said apparatus comprises a neuronal input. Optionally, said input comprises a spatially discrete input. Alternatively or additionally, said apparatus comprises a neuronal output. Optionally, said output comprises a spatially discrete output.

In an exemplary embodiment of the invention, said apparatus comprises both a neuronal input and a neuronal output. Optionally, said payload generates an input signal for said network. Alternatively or additionally, said payload receives an output signal from said network.

In an exemplary embodiment of the invention, said payload comprises an artificial organ. Alternatively or additionally, said payload comprises circuitry that performs a function for said network based on an input from said network and provides an output to said network. Alternatively or additionally, said payload comprises at least one of a localization device, a communication device and a general purpose computer. Alternatively or additionally, said payload comprises circuitry that detects a condition in said network and generates a signal to said network such that a response of said network to said signal will have a desired effect responsive to said condition. Optionally, said condition is an epilepsy attack and wherein said response is prevention of a propagation of said attack.

Optionally, said payload comprises circuitry that uses said network to perform a function based on an input from said circuitry and reading an output from said network.

In an exemplary embodiment of the invention, said apparatus is implantable. Alternatively or additionally, is wearable.

In an exemplary embodiment of the invention, said apparatus trains said network to have said input or said output area.

There is also provided in accordance with an exemplary embodiment of the invention, a method of assaying a drug for psycho-active effects, comprising:

training a neural network under a first condition of the drug and measuring at least one parameter related to the training;

training the neural network under a second condition of the drug and measuring said at least one parameter; and comparing the measurements. Optionally, said training comprises training by stimulus removal. Alternatively or additionally, said neural network is an in-vivo network. Alternatively, said neural network is an in-vitro network.

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which:

FIG. 13B shows records from three electrodes, each trace within a panel shows recordings obtained 100 msec before the stimulus to 100 msec after the stimulus;

FIG. 14B (right four columns) shows the change in R/S of the selected and control electrodes in four such experiments.

DETAILED DESCRIPTION OF EXEMPLARY EMBODIMENTS

OVERVIEW OF BASIC TRAINING PROCESS 18
VARIATIONS IN TRAINING 22
SELECTION OF INPUT AND OUTPUT SIGNALS AND PARTICIPATING NEURONS 25
TYPE OF OUTPUT SIGNAL 26
RETRAINING AND EXTINCTION 27
EXEMPLARY TRAINING SEQUENCE 27
NON-BODY APPLICATIONS 28
IN-VITRO DRUG SCREENING 29
IN-VIVO DRUG SCREENING 29
APPLICATION FROM OUTSIDE A BODY 30
INTRABODY APPLICATIONS 31
BASIS OF BRAIN TEACHING TECHNIQUES 31
EXEMPLARY AREA STIMULATION SIGNALS 32
EXEMPLARY TRAINING SETUP 33
EXEMPLARY TRAINING SESSION 34
EXEMPLARY PATTERN TRAINING 36
BROKEN-DOWN TRAINING OF PATTERNS 37
USER AWARENESS LEVEL 39
TRAINING AUTOMATION 40
UNLEARNING AND EXTINCTION 41
SEARCH RANGE 41

GENERAL STIMULATION BASED TRAINING 42
PREVENTING DESTABILIZATION 43
COMBATING SIDE EFFECTS 44
EXEMPLARY APPLICATIONS 44
AMBULATORY TRAINING DEVICE 45
MOTOR CONTROL 45
SENSORY TRAINING 49
COGNITIVE TEACHING 49
INPUT/OUTPUT INTERFACE 50
BYPASS INTERFACE 52
EEXEMPLARY DEVICE CONFIGURATIONS 53
BRAIN AS I/O INTERFACE 53
ADDING CIRCUITS 54
EPILEPSY TREATMENT 56
NEW BRAIN AREAS 57
REHABILITATION 58
PAIN 60
BRAIN ORGANIZATION 61
BRAIN CONTROLLER 62
NON-BRAIN APPLICATIONS 62
DIRECT HUMAN INTERFACE AND REFLEXIVE APPLICATIONS 63
TREATMENT OF VARIOUS DISORDERS BY VAGUS NERVE CONTROL 64
NON-HUMAN APPLICATIONS 65
EXPERIMENTAL DATA 65
METHODS OF THE EXPERIMENTS 71

Overview of Basic Training Process

Figure 1:
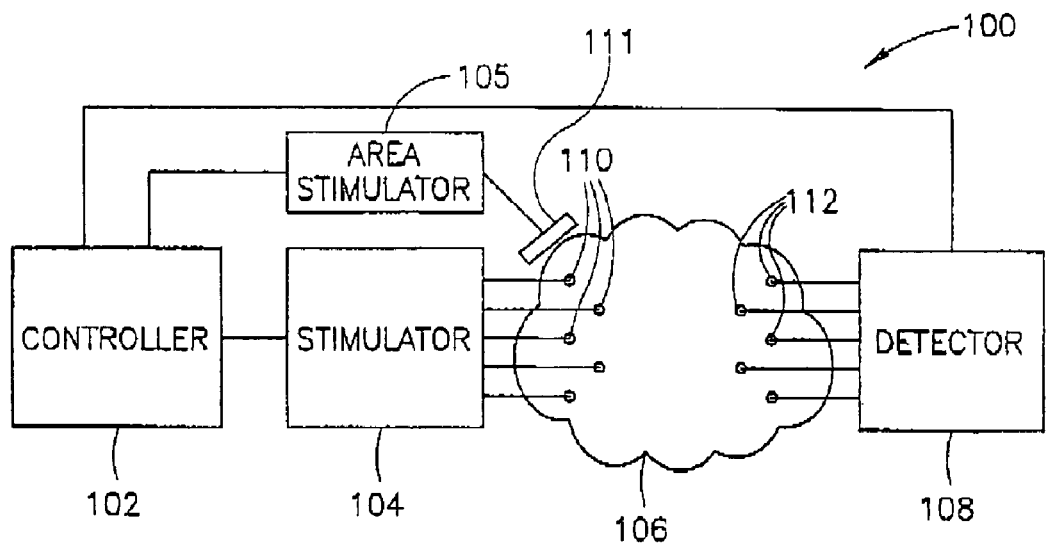
FIG. 1 is a schematic diagram of a system for training a neural network, in accordance with an exemplary embodiment of the invention.

FIG. 1 is a schematic diagram of a system 100 for training a neural network 106, in accordance with an exemplary embodiment of the invention. In an exemplary embodiment of the invention, system 100 comprises a controller 102 that controls the training, a stimulator 104 that, under control of controller 102 applies stimulation pulses to one or more electrodes 110, in neural network 106. A detector 108 receives activation indications at one or more electrodes 112, responsive to the stimulation at electrodes 110. These indications are forwarded to controller 102 for determining what stimulation to apply and/or its timing, for example as described below. Electrodes can be of any known types, such as, for instance, metal wires, bundles of such, arrays of such with various dimensions, printed circuits, nano-tubes, arrays of such, solution-filled tubes, arrays of such. As will be noted below, stimulation and/or detection means other than electrodes may be used. In various embodiments of the invention, neural network 106 is inside or outside a body, artificially grown or naturally occurring.

Optionally, an area stimulator 105 is used to selectively excite a portion of network 106, for example, the part of the network in which learning is to take place. Optionally, an external magnetic stimulation coil 111 is used. Alternatively, other physical stimulation methods may be used, for example, ultrasound. Alternatively or additionally, chemical stimulation methods are used, for example, stimulants, sedatives, neurotransmitters and/or their antagonists. In an exemplary embodiment of the invention, the training is applied under stimulating conditions (e.g., noise, light), which can be controlled, to reduce the stimulation level. Alternatively or additionally, a method of active reduction of the stimulation level is used.

In an exemplary embodiment of the invention, the following model of learning in neural networks is utilized. Any neural network includes stable connections and unstable connections. The stability of a connection may change over time. When a network is trained, some of the unstable connections are made stable, in a manner that will result in the correct response to a stimulus. The following stabilization method is postulated: when the network is stimulated, the unstable connections fluctuate, generating changes, which may be lawful, seemingly random, or truly random, in the responses within the network. This is termed "exploration" in that the network is exploring possible responses to the stimulation. The range of output patterns that may be discovered during the exploration is very large. Generally, if the stimulation continues for a sufficient period of time, one of the output patterns is expected to be an approximation of the desired output pattern. However, when the stimulation stops, some of the unstable connections, that allowed the exploration and generated the output signal, turn into stable connections, thus, permanently reconfiguring the network into a trained state.

Moreover, at least for some neurons (e.g., the rat neurons described below), an additional stabilization mechanism is postulated. The inventors have postulated that short periods of stimulation (e.g., under 2 minutes, or under 20 seconds) appear to stabilize the coupling between neurons rather than destabilize the coupling. When an exploration works and the stimulation is stopped, the short period of stimulation strengthens the couplings that made the exploration work, while other couplings, which experience a longer stimulation, are destabilized. It is hypothesized that neurons contain a coupling agent that is required to be at at least a minimum level in order to maintain a coupling stable. If the agent is at too high a level, for example caused by over-stimulation, the coupling becomes unstable. If the level becomes too low, the connection also weakens and becomes unstable. If there exists a mechanism for degrading or storing the agent, a low level of stimulation of the neuron and/or coupling may release additional units of the agent, that maintaining the agent level in a range that maintains coupling stability.

While the description focuses on stopping the stimulation once learning is shown, in some embodiments of the invention, the stimulation is changed rather than stopped, for example, its amplitude reduced, its parameters changed and/or stopping or changing of only one of a general stimulation and a specific stimulation. It is hypothesized that such change will have the property of reducing stimulation of "successful" couplings and/or maintaining a minimum stimulation level (and/or rate) that ensures stability of the couplings.

It should however be appreciated that the above theories and hypotheses are not necessarily correct nor are they required for operation of the invention. The theories may be partially correct as well, for example, the short-stimulation stabilization theory may be incorrect for some or all neuron types.

Figure 2:
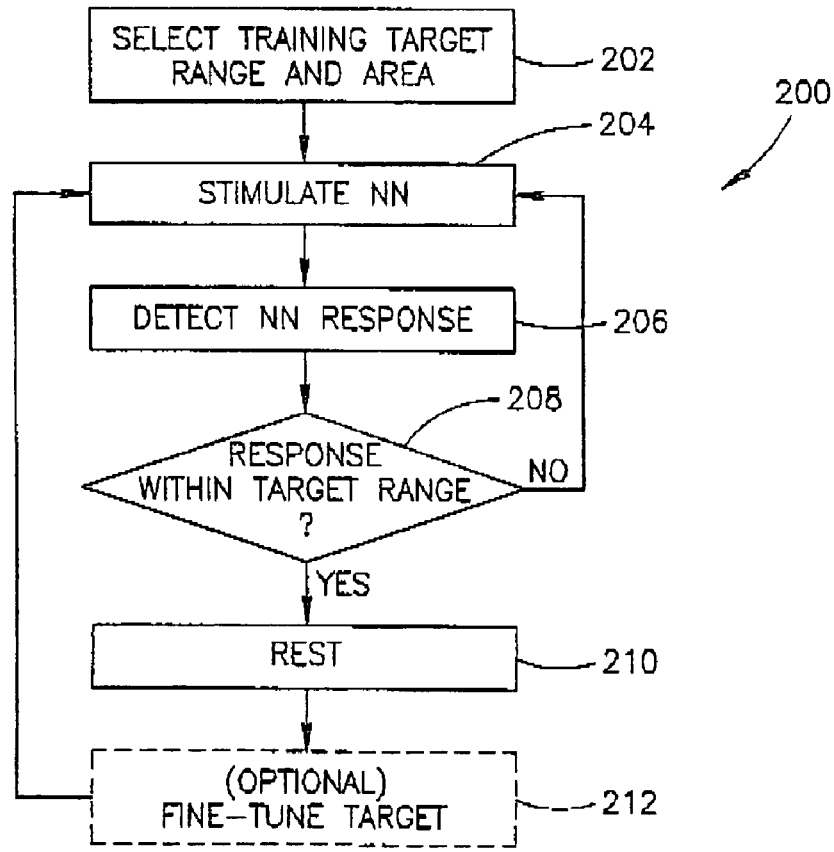
FIG. 2 is a flowchart of a method of training a neural network, in accordance with an exemplary embodiment of the invention.

FIG. 2 is a flowchart 200 of a method of training a neural network, in accordance with an exemplary embodiment of the invention, which utilizes this model. At 202, the training target area and target range are determined. The target area defines a neuron or neurons that can be expected to respond in the desired manner when the network is trained. The target range defines the range of a measured parameter that is expected to fall within a desired range when the network is trained. In an exemplary embodiment of the invention, the target area comprises one or a few neurons and measured parameter is a time window within which the target area is to have a desired response, for example, action potentials. As will be explained below, the target range may be selected as part of a training protocol for achieving a particular output signal.

At 204, an input stimulus is applied to the neural network. While the following description focuses on the brain, as a neural network, other neural networks and non-motor networks (e.g., in the stomach) may be trained using this method and the examples described below.

The stimulus may be a single stimulus that mimics the input signals to which the neural network should learn to respond with the above desired response. Alternatively, a two part stimulus may be used, an input signal stimulus part and a general stimulation part, which may have the general effect of destabilizing connections in the neural network. The general stimulation part of the stimulus may be applied before, during or after the first part. It is expected, in some embodiments of the invention, that the input signal stimulus has a destabilizing or training effect on neurons that are linked together functionally. The general stimulus is expected to have a destabilizing effect on a spatially-near set of neurons. In some cases, the general simulation is applied to a large part of the brain, or to the whole brain. the general stimulation may be, for example, less localized, for example directed generally to an area that is expected to be trained. Alternatively or additionally, the general signal is varying or otherwise less specific than the input signal.

At 206, the response of the neural network is detected. Various means, for example as described below, may be used to detect the response. The response may be that of a single neuron or of a group of neurons. The response may be one dimensional, for example, a time of peak firing, or multi-dimensional, for example, a spatio-temporal firing pattern.

At 208, a determination is made whether the detected response is within the target range. If not, the stimulation is repeated (or continued). In some embodiments, a plurality of ranges are provided, for example, one range being a time range and one range being a pattern range. If either range matches, it may be considered a match, with further training continuing on the matched and/or the unmatched range. In some cases, the range is defined as a function, with a distance from the function, for example, a correlation value of the network output with a desired output. Other functions may be provided as well.

If the response falls within the target range the stimulus is stopped and the neural network is allowed to rest (e.g., optionally reducing and/or stopping one or more other stimulus or environmental signals that cause excitation of the network). One or both of the input stimulus and the general stimulus may be stopped, in various embodiments of the invention. In one example, the input signal is continued and the general stimulus is stopped.

After the rest period, the target range is optionally fine tuned (212). For example, the target range may be narrowed by 10%, 30%, 50%, 80% or any smaller, greater or intermediate value, each cycle. The range may be widened or not narrowed some cycles, for example, if the network stops improving or if it shows signs of instability (e.g., increase in random responses). In some sequences, for example, the target range narrows using a linear, quadric or exponential function. Various "search methods", known in the art of linear programming, optimization problems and function solving, such as hill climbing may be used in setting and modifying the target range, with the goal of "finding-" (e.g., the network responding to the input with-) a correct output. In using these methods, the input is repeated and each time a better output is found, an evaluation of the target function is considered to have been made. In an exemplary embodiment of the invention, unlike traditional hill-climbing methods, the input is not modified. Instead, the repetition is considered to be a change in the input in "the best" direction, with the result being considered to be a local maximum or a ridge (or saddle). When no further improvement is achieved (e.g., using methods of statistical analysis known in the art), a local hilltop is assumed to have been found. If the hill-top result is still not good enough, a new starting point may be needed. Such a point may be provided, for example, by unlearning part of what was learned, changing the input pattern, choosing a different part of the network and/or stimulating the network with various parameters. Alternatively, since a desired output may be achieved by approaching using different sequences of (changing) input patterns, each input pattern starting point may be considered to be a different point in space. One possible complication is that there may be interactions between one training session and another. These interactions may be, for example, ignored or provided for by suitable processing of the results and/or by selecting and arranging the starting points to be as dissimilar as possible.

The process of stimulating, testing and resting may be repeated multiple times, for example, until the response is stable and/or the target range is as desired. The stimulation cycle can be repeated, for example, 2, 5, 10, 20 or any smaller, intermediate or greater number of times.

If the response does not fall within the range, the stimulation is repeated and/or continued (e.g., depending on if a continuous or discrete stimulation is used). Optionally a short rest period is provided between stimulations, for example to prevent over stimulation or tiring out of the trained neurons. For example, a delay of 1, 30, 50, 10, 100, 1000 or any smaller, intermediate or larger delay may be provided. Additionally or alternatively, the amplitude of stimulation may be modified, for example cyclically. Alternatively or additionally, the exact stimulation may be changed, for example, temporally and/or spatially.

Variations in Training

The above training process can be varied in many ways. For example, the network may be trained for multiple target areas and/or target ranges and/or input patterns. Such training may be in parallel, in series, or interleaved, for example, with different target ranges being alternated between sessions. Alternatively or additionally, a same set of neurons is trained for responding to multiple different input signal sets.

Another exemplary variation is replacing the rest period by a repetition of the training session at a lower intensity, so that fewer neural connections will be destabilized. Alternatively, the general stimulation signal is reduced or removed. In an exemplary embodiment of the invention, the general stimulation signal intensity is reduced as the achieved output signals approximate the desired output, for example, in a continuous or a step-wise manner.

Alternatively or additionally, hyper-polarizing electric fields, temperature variations, medication or various biochemically-active substances may be used to increase or reduce neuronal and synaptic stability, thus replacing or supplementing rest periods and/or increasing effectiveness of stimulation sessions. In an exemplary embodiment of the invention, an implanted catheter or drug eluting device is used to provide chemicals in the brain for such use. A wireless-controlled pump may be implanted for example.

Optionally, what is blocked is not the activity of a neuronal area, but the propagation of signals to that area. For example, an input image stimulation may be stopped by preventing propagation from one visual cortex area to another or to a non-visual processing area, for example, using methods well known in the art. This allows an artificial modulation of input even if the input itself cannot be controlled. Rather than blocking, modulation and/or modification of the input may be used instead.

The stimulus may be a constant stimulus or it may be varying. Further, the stimulus can be spatially or temporally varying.

As noted above, the "rest period" need not be a cession of all stimulation. Rather, the input signal may continue. Alternatively, "rest" is provided by directing the training to a different part of the neural network and/or to a different pattern. Further, application of a small amount of stimulation during the rest period, for example periodically, may be used to prevent the learning from becoming entrenched on fine points of the input signal, by prevent the learning from being too exact. Alternatively or additionally, various stimulation parameters and/or types may increase the stability of the network. Such parameters may be found by testing a particular network or network class, storing the parameters and then using them during training to modulate retaining and/or stability of a network.

Various training schemes can be used, for example, first forcing the response to be a unique outstanding response in a range (e.g., of time, intensity and/or frequency) and then forcing the response to be within the desired target window range. Another exemplary training scheme is first forcing the response to include a response in the window and then force the response to be only in the window. Another exemplary training scheme is to limit the response to the window, adjust the response to be as desired and then again limit the response to the window. This process may be repeated, iteratively.

The repeated signal may be the same as the previous signal. Alternatively the signal is varied, within a cycle or training-rest and/or between cycles. For example, such varying may be used to progressively provide a finer pattern to be learnt. Alternatively or additionally, the progression may be random changes, to ensure that a more generalized pattern is learned. Alternatively or additionally, the varying may be in response to the network's instant and/or previously determined ability to learn. For example, parts (or types) of the pattern to which the network is responding better, may be fixed (e.g., to focus learning on other parts of pattern) or purposely varied (e.g., to take advantage of the ability of the network for that part of the pattern), or vice-versa for parts or types of patterns with which the network is experiencing difficulty.

The neuronal property that is being measured can be of various types, for example, one or more:

(a) absolute or relative response intensity relative to surrounding neurons;
(b) response intensity relative to input;
(c) delay from stimulus to response;
(d) temporal wave form of response, e.g., decay time;
(e) spatial form of response; and/or
(f) degree of variation of response.

As will be noted below, in some embodiments of the invention, what is measured is not the neuron output, but its effect, for example, a feeling sensed by a human in whose body the neuron is acting or an output effect on the body, such as a glandular secretion.

The measured responses may be, for example, signals from parts of a single neuron, or whole neuron responses, or groups of neurons and/or groups of neuronal related activities.

When a target range is defined, it is optionally exclusive, in that no response (e.g., above a threshold) is allowed outside the range and/or near the boundaries of the range. Alternatively or additionally, the range may be limited to requiring a response that includes a component inside the range. Alternatively or additionally, the range may be open at one end thereof.

Optionally, instead of defining the range as a fixed range, the range is defined as a function of the input.

Optionally, the target response range is defined as a function of one or more previous stimuli as well or instead of being a function of a present stimulus. In an exemplary embodiment of the invention, training such a pattern comprises defining a set of temporal patterns of input signals and training for them in sequence. Optionally, after every few input patterns, a previously trained input pattern is re-trained, to ensure that it does not get erased by the new training.

The target area can be small or large, for example, including one, ten, 100, 1000 or more neurons or neuron ensembles. As the number of neurons in the target area increases, more complex responses from an area can be expected and/or achieved. In some applications, synchronized signals from large areas may be easier to detect, for example, being stronger, more sustained and/or temporally and/or spatially patterned in a desired manner. In an exemplary embodiment of the invention, the response of a large area comprises an accumulation of momentary responses of subsets of the neurons, with different subsets responding at different times, so that a more sustained response is received. An additional potential advantage of large target areas is that they may be more robust, in terms of resistance to neuron loss. On the other hand, in some cases, it may be easier to train individual neurons and/or the training thereof may be more exact. Similar sizes may be used for the input areas.

In some cases, behaviors are not mapped to single spikes generated by any one neuron, but rather to groups of spikes. These groups of spikes, neural activity groups, may originate from a single neuron or from populations of neurons that are firing in synchrony or diachrony.

In an exemplary embodiment of the invention, the input area and the target area are within a function module of the brain, however this is not required. As will be explained below, the input and target areas may even be on opposite sides of the brain. In an exemplary embodiment of the invention, the distance between the input area and the target are is, for example, 10, 100, 1000, 10000 microns or any larger, smaller or intermediate distance.

Optionally, the training process includes a determination of whether the training is proceeding as expected. For example, whether the network is converging fast enough to the target range, whether the training is being retained and/or the effect of multiple post-training stimuli and/or training to other stimuli on the retention. Possibly, the training scheme is modified responsive to the measured responses and/or progression, for example in response to an indication that a certain training method and/or stimulus range is achieving desired training results. Alternatively or additionally, in some applications, the target range and/or stimulus range are modified to match values that are more easily learnt and/or retained by the network.

Selection of Input and Output Signals and Participating Neurons

In an exemplary embodiment of the invention, when a plurality of input and output areas are available for training (e.g., using an electrode array) the neurons actually trained are selected from the plurality of available neurons/input areas. In an exemplary embodiment of the invention, the selection is based on the neurons amenity to be trained and/or retain training, quality of coupling between the input signal generator and the input area and/or that their training does not have adverse effects on the training of other patterns or the brain as a whole.

Alternatively or additionally, a determination is made to see what types of patterns may be easily learnt by the neurons being trained. The patterns actually taught may be selected based on what the network is more amenable to learning and/or retaining. A particular example is negative vs. positive patterns, which may depend on the ratio of and/or whether excitatory or inhibitory neurons are being affected by the training. In one example, neurons which show inhibitory or excitatory patterns are maintained and/or dropped based on a desired type of neuron for a certain electrode for a distribution for a group of electrodes. Generally, it is easier to reprogram the electrodes rather than change neurons. In an exemplary embodiment of the invention, more than a minimum required number of neurons are connected to, so that some play remains.

The inventors have found several rules of thumb that may be useful in determining the suitability of neurons (e.g., electrode placement). In some cases, of course, one or more of the rules may need to be ignored, in order to achieve desired results. One such rule is that neurons that exhibit an initially weak response are more malleable (or their couplings are) in training. In application, electrodes will be selected if the response to an initial stimulation is weak or if it is strong and close to the desired response. Another such rule is that neurons tend to not change the polarity of response change (e.g., once the neuron shows a change in a certain direction as a result of training, that change direction is likely to be maintained for relatively long periods of training). In application, neurons that respond in opposite of the desired change direction are not used. A third such rule is that many, but not all neurons quickly show improvement as a result of training. In application, a neuron is dropped if no (or small) positive training result is shown after one or two sessions. Some neurons are "late bloomers", in which the number of sessions required to show a training response is larger than one or two. A fourth such rule is that strong connections should be (and generally will be automatically) stimulated for short periods of time. In application, this rule may be used to determine if a training session is not progressing.

In an exemplary embodiment of the invention, before embarking on a long training session, the connected to neurons are tested using a short, related or unrelated training sequence, to determine their suitability and/or flexibility. Depending on the results, some or all of the neuronal connections may be replaced and/or the training sequence may be changed.

Type of Output Signal

In an exemplary embodiment of the invention, the training is directed to generating a certain steady output signal, possibly with a certain spatial pattern. The steady signal may have a window defined, which window is selected to be after a relative steady state is achieved.

Alternatively or additionally, the training is directed to achieving a temporal pattern. Optionally, the pattern includes (or is completely) within times where the neural network is not yet stable. Alternatively or additionally, the spatial patterns which are trained are patterns generated during an unstable period of the neural network.

As has been shown, for example in Amir Toib, Vladimir Lyakhov and Shimon Marom, "Power law relations between activity and availability of the mammalian brain Na channel", J. of Neuroscience, 18:1893-1903, 1998 and Dror Tal, Eyal Jacobson, Vladimir Lyakhov and Shimon Marom, "Frequency tuning of input-output relation in a rat cortical neuron in-vitro", Neurosc. Lett., 300(1):21-24, 2001, the disclosures of which are incorporated herein by reference, the response times and refractory periods of individual channels, synapses and neurons may be affected by previous activation of the neurons. Thus, in an exemplary embodiment of the invention, as the neural network is trained, both the steady state and the unstable states of the network can be modified by the training process.

While some of the effects of training are short term, In an exemplary embodiment of the invention, long term effects on the brain are achieved. As is known, the brain continuously adapts to its changing needs. In an exemplary embodiment of the invention, the training is used to force the brain to adapt in a certain way, for example to exercise certain parts of the brain. Possibly, this may cause one or more of neuronal growth, migration, new cell formation (neuronal, support and blood vessels) and/or extension of dendrites. In an exemplary embodiment of the invention, a new channel is created by progressively creating interactions between neurons that are connected, until a complete path between unconnected neurons is created. Such a path can also be built up in parts that are later connected. While such a path may be contiguous in the brain, this is not required, considering the high connectivity between brain areas.

In an exemplary embodiment of the invention, when modeling of the brain is desired, periodic feedback on the effect on the brain of the training is provided, for example, using functional MRI or other imaging or EEG studies. This feedback may be provided outside from the device (EEG can, of course be provided on the device). The training applied may be changed, if needed, for example, manually or automatically. Alternatively, feedback is provided by determining a desired change in an activity of the brain, for example, a change in learning time or a change in a degree of rhythm of activity.

Retraining and Extinction

Optionally, extinction causing sequences, for example, randomly occurring stimulation sequences which "train" the network to have a different response to the same stimulus by random stopping of the stimulus, are tracked, to determining if retraining is required. Alternatively or additionally, periodic retraining may be applied, for example based on a response to a test stimulus or based on tables of periodic retraining determined by experience with this or other networks.

Exemplary Training Sequence

Figure 3:
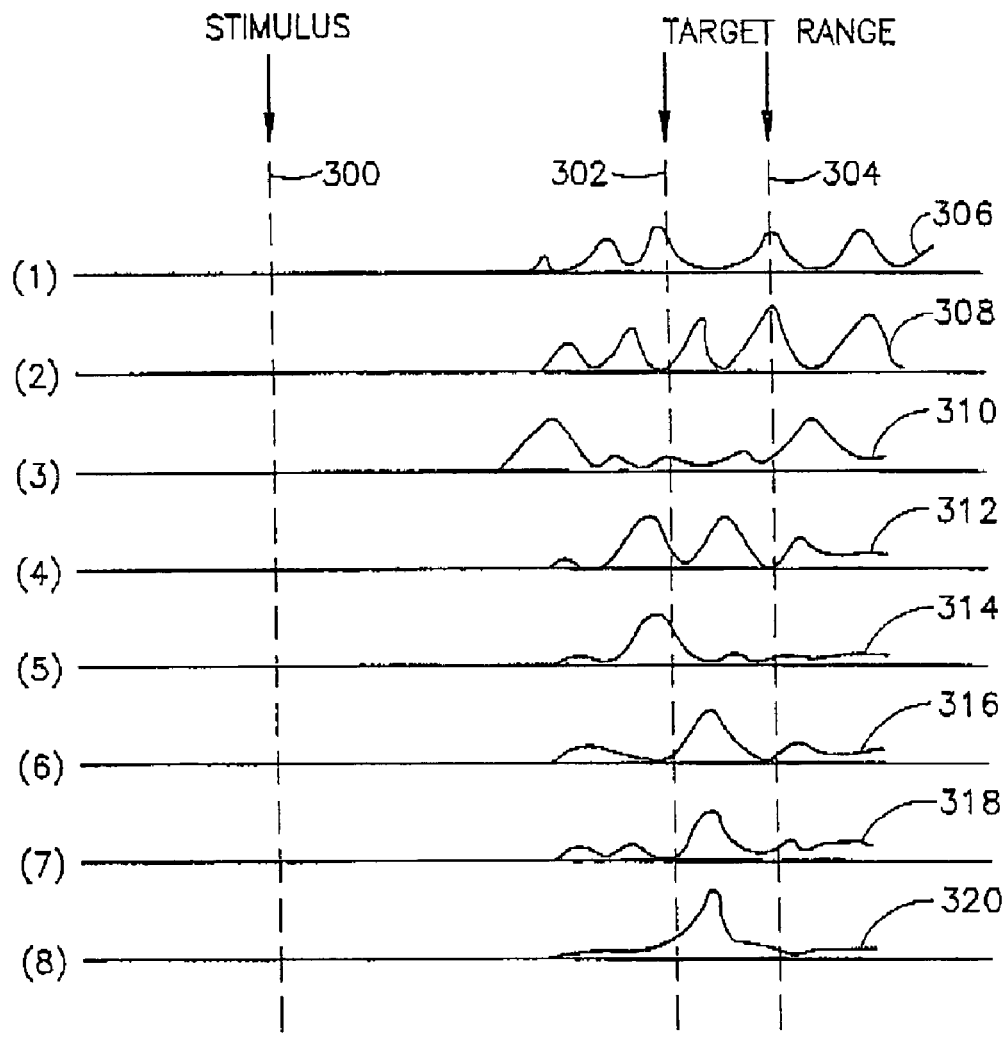
FIG. 3 is a schematic diagram shown exemplary input and output signals that can be achieved using the apparatus of FIG. 1 and the method of FIG. 2.

FIG. 3 is a schematic diagram shown exemplary input and output signals that can be achieved using the apparatus of FIG. 1 and the method of FIG. 2. The diagram shows eight aligned time lines, which represent results from selected trials. Reference 300 indicates the application of a stimulus signal to a first area of network 106. References 302 and 304 indicate a time window range within which a response is desired.

At a first trial, a response 306 does not even include a peak within the range. At a later trial, after multiple attempts, a response 308 includes a peak aligned with the window. A rest period is then initiated, after which, at a later trial, a trace 310 shows that the previous achieved result is not yet repeatable, however, the response shows a temporal variation that might be useful. At a later trial, after still further attempts, a trace 312 has a peak that is aligned with the window. Later trials (with possibly intervening failed trials) yield traces 314, 316, 318 and 320, that show further refinements of the response, where rest periods may be initiated after one or more of these relatively successful trials.

In some applications, for example where the output signal is spatially modulated, the input stimulus may be continuous (e.g., DC or at a frequency higher than the neuron response time), rather than discrete or periodic.

In an exemplary embodiment of the invention, EMG will be measured from several muscles and a criteria be defined describing the activity to be achieved (e.g. contraction of a specific muscle with no activity of other muscles). Then, a motor area which is not directly connected with these muscles (e.g. the SMA) is stimulated. The stimulus will be repeated until the learning criterion is achieved (e.g. the pre-defined muscle contracts in response to the stimulus) and then withheld for relatively long time period. The protocol will be repeated until stable association is formed.

EMG is optionally used as it can be detected in real time and used to control the stimulation system in a closed loop manner without relying on subjective reports of the subject or on much noisier EEG recording. EEG is optionally recorded during the experiment analyzed, for example, to characterize the functional changes induced by the learning protocol.

In an exemplary embodiment of the invention, the analysis includes analysis of correlation of oscillatory activity between the brain and the muscles and between different brain areas in order to characterize the connectivity changes induced by magnetic stimulation. This 'coherence analysis' technique has been developed in recent years and has been successfully applied in various studies.

Non-Body Applications

In an exemplary embodiment of the invention, the above training method is applied to a neural network that is outside a living body. Although various training patterns are described below, a particular ex-vivo application is the training of a neural network computer, e.g., one which includes living neurons that are grown in a suitable solution. Other exemplary devices include neurons grown on a electronic substrate and hybrid devices that combine electronics and neural networks.

In-Vitro Drug Screening

Another exemplary application is screening of CNS-affecting drugs. Such drugs can include those which have a CNS side effect, which screening is designed to find, and also drugs whose CNS effect is a main effect, for example memory enhancement. In an exemplary embodiment of the invention, such effects are determined by comparing a control network group and a drugged-treated network group, for example to detect changes in training speed, training retention, training curve shape, number of patterns that can be retained per unit and/or plasticity. The same network can be used to test the above drug effects e.g., a within network experiment.

Figure 11A:
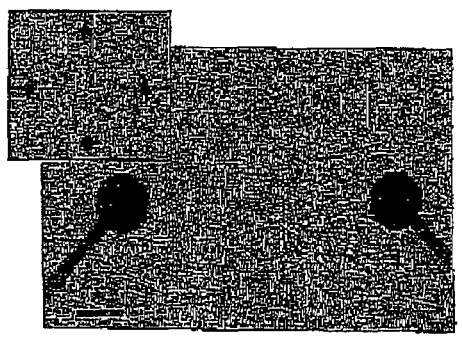
FIGS. 11A-11D illustrate a cortical network and various statistics measured thereon, in an experiment in accordance with an exemplary embodiment of the invention.

In an exemplary embodiment of the invention, a drug-screening device comprises a system such as shown in FIG. 1 and FIG. 11a, with the neural network being provided on a suitable growth substrate and the controller appropriately programmed. The growth substrate may be covered by a complete array of electrodes, for example, to allow access to any part of the network and allow reusing the network if desired.

In vivo and in vitro cognitive screening may also be used to determine the effect of therapy, RF radiation, training methods, sleep depredation and/or environment, for example.

In-Vivo Drug Screening

In an exemplary embodiment of the invention, drug screening is performed on a living test subject, for example, a human or an animal. In such screening, the effects of a drug can be compared within the same subject, over a time period and/or compared to other drugs. In an exemplary embodiment of the invention, an array or a bundle of electrodes is implanted in the subject and at least some of the electrodes or other means of stimulation are used for imposing a pattern on the brain (or neural tissue). The above-mentioned parameters may be used to assess the effect of the drug on the learning ability of the brain. Optionally, one or more neurotransmitter sensors are implanted as well, for example, to assist in determining the simultaneous affect of the drug on such neurotransmitters.

In an exemplary embodiment of the invention, a device for animals is implanted or partially implanted and work on the animal (e.g., a collar, or sticking out of the head). Alternatively, an external device connected by wires to the animals may be provided. A baseline behavior for the animal and/or the particular location trained may be acquired. Thus, within animal testing, even of different dosages may be provided. Alternatively or additionally, between-animal testing is provided.

In an exemplary embodiment of the invention, a single electrode is used for detection. The training is desired (to the extent that the drug does not interfere), to change the statistical behavior of action potentials recorded by one electrode following the stimulation.

Alternatively or additionally, a field potential is detected. Field potential statistics in general may not change for some training sequences, e.g., beyond typical changes in the level of activity measured externally (blood flow, EEG) when cognitive activity takes place. On the contrary, in some cases, such change is undesirable, as rapid stimulation may, in some case, lead to inactivation of the network. However, it is expected that an effect can be detected when decomposing the signal (e.g. by Principle Components Analysis)—where a specific component may change its statistics, thus indicating changes in the routing and/or signal propagation within the network.

Alternatively or additionally, EEG signals are detected. This may be used, for example, when dealing with mapping of a biological sensor (e.g. whiskers). In an exemplary embodiment of the invention, EEG is sufficient for analysis of the response of an area (e.g., by LORETA—low resolution electromagnetic tomography technique). This technique can allow visualizing the exact location and time course of neural activity and can be extremely useful in studying the responses of the brain to TMS and finding areas involved in task related processing. Such localization may be helpful in finding the best stimulation sites.

Alternatively or additionally, EMG signals are detected. For example, changes in the overall power (amplitude, energy, frequency), or changes in the statistics of the pulses (timing relative to stimulation) may be of interest.

Application from Outside a Body

As will be described below, an in-vivo neural network can be trained without any invasive procedures. In an exemplary embodiment of the invention, an in-vivo neural network is trained without any direct contact with CNS nerves, rather, using only peripheral nerves. Alternatively, for example, external stimulation, such as using TMS (trans-carnial magnetic stimulation) is used.

In an exemplary embodiment of the invention, an ID prompt-response sequence is trained into existing neural networks. Such an ID has the useful properties that a person is always carrying it around and that the person does not know the ID, so it cannot be easily stolen from him.

In an exemplary embodiment of the invention, the prompt-response sequence comprises a prompt generated by stimulating peripheral nerves, for example in the finger tip and the response is a motor response of the muscles, for example, at the same peripheral location.

In an exemplary embodiment of the invention, the training of the ID comprises placing a finger into a receptacle of a suitable device, stimulating selected parts of the finger tip, in a particular spatial and/or temporal pattern, and stopping the stimulation, when the desired temporal or spatial response is achieved. This training is repeated multiple times until the training is retained. Possibly, the ID utilizes other parts of the body and/or multiple fingers.

The neural network trained is the motor-network in the spinal column. In more complex ID's the motor centers in the brain may be involved as well.

The above methodology may also be used to train new reflexes, for example to replace missing reflexes and/or to add new ones.

In another exemplary application, functions of a damaged portion of a visual cortex are remapped/transferred to a different part of the visual cortex. In one example, a patient is shown a flashing spot in a fixed area of an otherwise blank visual field, until the patient reports a visual sensation. The stimulus is then stopped and repeated after a rest period (e.g., as in the training method described above). Optionally, the different part of the cortex is stimulated, for example, using chemical, physical (e.g., ultrasound) and/or sensorial means (e.g., showing a movie or a flashing filed). Optionally, it this general simulation that is stopped, alternatively or additionally to stopping the input of the flashing spot. Additional application for rehabilitation are described below.

Intrabody Applications

While intrabody applications may be completely non-invasive, for example as will be described below, these applications may include accessing internal neurons that do not have outside connections. For clarity, most of the following description focuses on the CNS and especially the brain. However, the following methods may also be applied to nervous plexuses and/or other neural networks in the body, for example the motor complexes of the GI tract.

Basis of Brain Teaching Techniques

The above training method allows an operator to impose a desired behavior on neurons. Further utilizing the properties of cortical plasticity, the functioning of the brain can be remodeled to various degrees. To some extent, such remodeling allows the brain (or part of it) to be treated as a configurable and programmable embedded device. For example, remodeling can include one or more of:

(a) teaching new patterns in an existing brain area, of a "natural" form, for example, motor action patterns or language patterns;

(b) creating unconnected patterns, that the brain will later connect up;

(c) modifying connection statistics between different parts of the brain;

(d) creating functional relationships between parts of the brain that did not have an active relationship;

(e) creating a new functional brain area;

(f) imposing a teaching on the brain that is not normally achievable by regular teaching means, for example, teaching a cat to calculate;

(g) training the brain to control itself, in a desired manner; and (h) optimizing brain activity and/or providing a cognitive controller.

Furthermore, the imposed patterns may assist in creating a direct interface with the brain. Such an interface may be an interface between the brain and an input output circuit. Alternatively, the interface may be between the person whose brain it is and the brain, without intervening hardware.

Exemplary Area Stimulation Signals

Various stimulation methods may be used to destabilize connections between neurons, including, for example, one or more of:

(a) direct stimulation and/or inhibition of the neurons, for example, using electric, magnetic, electromagnetic or ultrasonic fields;

(b) indirect stimulation and/or inhibition, by different neurons that directly stimulate the neurons to be stimulated, for example, based on a previously trained pattern;

(c) chemical stimulation and/or inhibition, for example, systemic or locally applied neuromodulators (e.g. Dopamine);

(d) sensory stimulation and/or inhibition, for example, sounds, visuals (with or without content) and tactile stimulation; and/or (e) envelope stimulation and/or inhibition such as hunger, time of day, temperature and/or previous exertion.

Reduction of stimulation may be achieved, for example, by stopping such stimulation, or by counter-effects. For example, hyper-polarization of the neurons, indirect inhibitory effects by inhibitory neurons, sedatives, sensory deprivation and rest.

Exemplary Training Setup

Figure 4:
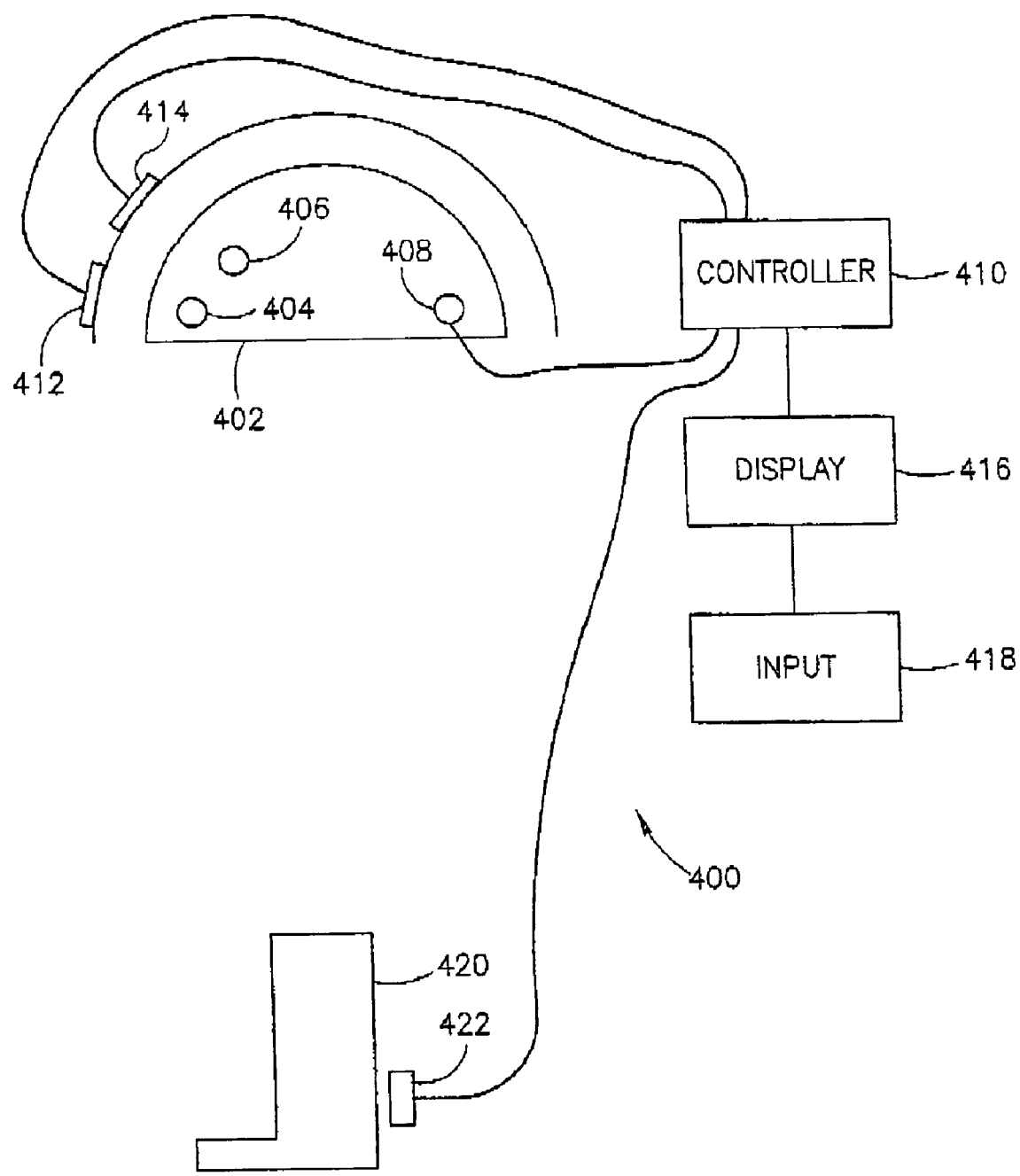
FIG. 4 is a schematic showing of a setup for training a brain, in accordance with an exemplary embodiment of the invention.

FIG. 4 is a schematic showing of a setup 400 for training a brain 402, in accordance with an exemplary embodiment of the invention. Setup 400 includes a stimulator 412 for stimulating a region 404 of brain 402 and a detector 414 for detecting a response of a region 406 of brain 402. A controller 410 is optionally provided to control the stimulation and/or process data from detector 414. Controller 410 optionally includes a display 416 and/or an input device 418, for an operator, if any or for the trainee, for programming purposes or if he is awake.

In an exemplary embodiment of the invention, detector 414 comprises a non-invasive detector, for example a SQUID array. Alternatively or additionally, invasive detectors, for example electrodes and embedded, wireless electrical sensors, may be used.

Stimulator 412 may be of any type known in the art, for example, non-invasive magnetic or ultrasonic stimulators or invasive or non-invasive electrodes.

An example of an electrode is shown schematically as a line connecting a brain region 408 with controller 410.

In some applications, electrodes may already be implanted in the brain, for example, in some epilepsy patients.

Alternatively or additionally to a detector in brain 402, an effect of stimulating a region 404 may be detectable by an effector sensor 422, for example, which sensor detects a response of an appendage (e.g., a limb, such as a leg) 420 or other part of the body. Feedback at appendage 420 may be slower than feedback at remote (from 404) brain region 408, which itself may be slower than feedback from nearby (to 404) brain region 406.

The sizes of regions 404, 406 and 408 and the resolution achieved for stimulation and readout in these regions is typically limited by the technology used. For example, implanted electrode arrays will generally have a better resolution and localization ability than external magnetic stimulation and SQUID readout. For example, TMS (trans-cranial magnetic stimulation) magnetic stimulation currently has relatively low resolutions, while intra-cranial electrodes have a readout resolution that is greater than the TMS stimulation resolution. For example, implanted electrode arrays can be directed to stimulate (and/or read) areas or even individual neurons. High-resolution EEG and TMS currently have resolutions of about 1 cm.

However, in some embodiments of the invention, the temporal resolution of the response and/or the complexity of the response are used to compensate for the reduced spatial resolution of stimulation and readout regions.

In an exemplary embodiment of the invention, detector 414 is a detector that can detect motor patterns, for example, as described in the above referenced, "Real Time prediction . . . ". Such a detector, possibly in conjunction with a suitable programming of processor 410 can be used to associate meaning with detected patterns, for example, identifying a connection between a detected pattern and a particular motor pattern.

One potential problem with animal cortexes is their tight organization in which, for some cortical layers, most neurons that are neighbors inhibit each other, which stimulating neurons are often far apart. In one embodiment of the invention, this is dealt with by implanting many electrodes and selecting electrodes for neurons with sufficient excitatory connections (some inhibitory connections are often desirable). The typical geometries of inhibitory and excitatory neurons are well known (or can be visualized per cortical area and/or layer) and may be used as a basis for distribution of electrodes. In an alternative embodiment of the invention, use is made of excitatory channels that interconnect brain areas. For example, several such channels connect sub-cortical regions and the cortex or different areas in the cortex. Examples of suitable channels are those which connect the amygdala to sensory areas, those which connect the hippocampus to other parts of the cortex and those which connect the thalamus and the cortex. In an exemplary embodiment of the invention, the stimulation is applied at either side of the channels, for example, the sub cortical areas and sensing at the cortical areas (or vice versa) to assist in providing excitatory connections.

One exemplary configuration comprises a non-invasive stimulation system (e.g. TMS), with a control unit, which receives both the measurements and controls the stimulation. The control unit is responsible for induce and/or maintaining the learning process. The system may include a storage device for keeping the record of the specific patient, including information such as the calibration and history of treatments. The storage and the algorithm may be personalized, and may be implemented by a smart card (e.g., per patient). Optionally, the configuration includes a location (Navigation) system—for better positioning within the cortex, possibly using MRI, CT or any other imaging method (e.g., structural and/or functional imaging) for navigation.

Exemplary Training Session

Figure 5:
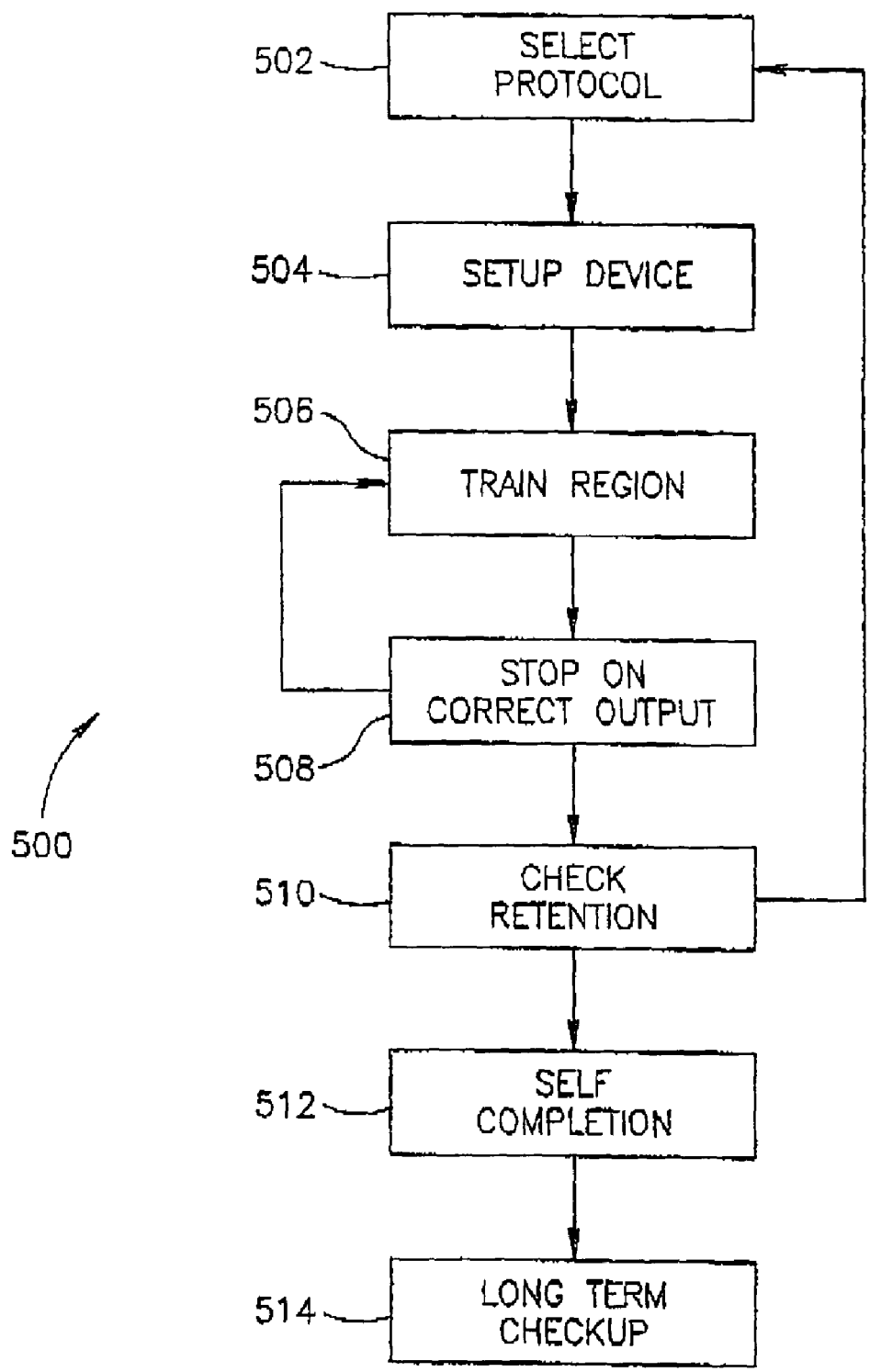
FIG. 5 is a flowchart of an exemplary method of training a user's brain, in accordance with an exemplary embodiment of the invention.

FIG. 5 is a flowchart 500 of an exemplary method of training a user's brain, for example, with a motor pattern, in accordance with an exemplary embodiment of the invention.

At 502, a training protocol is selected. This protocol may be based, for example, on the type of pattern to be trained (e.g., motor, sensory), on the complexity of the pattern and/or on indications from previous training sessions of the user or other users.

At 504, the user is fitted with a device, for example, as shown in FIG. 4. Optionally, the type of device depends on the protocol selected. It should be noted that regions 404 and 406 depend on the pattern and on the protocol. However, in some cases, for example motor pattern training, regions 404 and 406 may overlap or even be a same region.

At 506, the training is applied, for example, as described with reference to FIGS. 2 and 3. The exact details of the training will typically depend on the protocol selected, the pattern being trained and/or on the response of the user's brain to the training.

In an exemplary embodiment of the invention, the user's brain is trained to respond to an input from a different part of the brain (e.g., an instruction to flex a leg), with a particular motor output, for example, flexing of the leg. A user may be instructed, for example, to imagine flexing the leg, and the pattern generated by such a thought used as the input pattern to be applied during training. Optionally, the pattern is artificially applied. Alternatively, the user's imagination applies the signal during training. In an exemplary embodiment of the invention, the training effect is achieved by starting and stopping of a general stimulation signal, Alternatively or additionally, to controlling the input signal.

The output pattern may be selected, for example, to be a pattern which when connected to electronic effectors on a paralyzed limb, cause the limb to flex. Alternatively, the mapping between brain patterns and the effect on the effectors is also trained into the user.

At 508, a training session is paused or stopped when a correct response to an input is achieved.

At 510, an optional retention testing is performed. For example, a determination is made whether the training "took", for example, by testing if the user can apply the trained motor pattern. Alternatively or additionally, especially if another pattern is trained into the brain, a test is made to determine if the training of the multiple patterns interfere.

At 512, an optional self-completion step is performed, in which the user and/or his brain complete and/or fill-out the training, as described below. In some protocols, the user completion stage is an important part of the overall training process. To that effect, a user may be provided with a detailed series of exercises to perform and/or items to monitor, for example using a questionnaire, periodic checkups, periodic connection to an Internet site or an ambulatory device (described below).

At 514, an optional long term checkup is made, for example to monitor the training session results (e.g., retention, inference) or the desired effect (e.g., ability to use a paralyzed limb).

Exemplary Pattern Training

A training pattern typically comprises an input to be provided and an output that is desired in response to that input.

In an exemplary embodiment of the invention, the input is a natural input, for example, a direct sensory input signal. The output is a tangible output, for example, an activation pattern with a known effect and/or a response of a body part.

Alternatively, the input is a natural input, but not for the trained pattern. In one example, an input pattern that is normally directed to flexing a left leg is remapped for use in flexing the right leg. A potential benefit of such remapping is that prior to the training the input is known and can be both identified and activated at will by the user. The user can then learn a new pattern for flexing the left leg. Such remapping may also be useful in other applications, for example, to assist a user in remapping a visual cortex from a damaged part of the retina to an undamaged part of the retina.

A natural input can be naturally provided, for example, by the user thinking the correct thoughts or a sensory input provided. The training can be triggered to be activated once such correct input patterns are detected. Alternatively, once such a correct input activation pattern is detected, the input pattern may be artificially provided, for example, using electrodes. Alternatively, the user's brain is stimulated, at a different brain part, to generate the desired input signals. A suitable stimulation for generating the input signals may be determined by applying a plurality of different stimuli to the brain area that generates the input pattern, until the input signal pattern is generated. The correctness of the input signal pattern may be determined, for example, by comparing the signal to a recording of a signal pattern that is known to be correct, for example, by having the user generate the pattern by thought.

When the input and output signals have a natural meaning and/or functional connectivity to other parts of the brain, the pattern may be used as soon as it is trained. However, in some embodiments of the invention, the input and/or the output are not attached to meaningful functions. For example, the input signal may be unrelated to any existing input signals. Similarly, the output signal may be unrelated to existing output signals. Possibly, when the input and/or output signals are selected to match the capabilities of the sensing and/or stimulated means used, a matching to existing brain input and/or output signals must be forsaken. However, once the pattern is programmed into the brain, the brain can naturally "find" the pattern's inputs and/or outputs and create links for them. Thus, in some embodiments of the invention, the input and/or the output are selected to be artificial, rather than existing.

In one example, an artificial input signal is used to train a particular hand movement into a motor area of the brain (e.g., an artificial input, with a tangible output). Random activation of the brain (e.g., by having the user think random thoughts or perform a mental exercise that uses that brain area) will generally cause at least partial activation of that pattern at some time. Once even partially activated, the user, who is aware that the pattern is trained, can consciously strengthen the links, by using the link a few times. Alternatively, stimulation based "searching" for the pattern may be used, for example, with higher quality electrodes than used for training. Alternatively, an area stimulation may be used in the hope of causing the input pattern to be activated.

It should be noted that even when pre-existing inputs and/or outputs are used, the pattern trained often does not cover complete needs. Instead, in some embodiments of the invention, a minimal scaffold or skeleton pattern (or set of patterns) is trained. As the patterns are used and naturally varied by the brain, new patterns, covering a myriad of conditions are created. Possibly, the old, trained, patterns are forgotten, for example being unsuitable. In one example, a pattern for flexing of a leg to a cretin degree is trained. Once the user starts flexing the leg using the trained pattern, the brain will generate many more flexion patterns for different flexion degrees.

Such scaffolding and completion by the user is also useful when remapping a function to a new location in the brain. By remapping parts of the function (e.g., a sensory area), and practicing the user with those transformed patterns and near variations, the rest of the sensory area is naturally remapped to the new location.

Broken-Down Training of Patterns

Some patterns may be difficult to train in one go. For example, the delay until an approximation desired output is generated by stimulation of the neural network may be very long. In some cases, training will cover a plurality of sessions, for example, 2, 10 or 100, with each session, optionally, completing a part of the training. If an ambulatory device is used (as described below) training can be more continuous. Following are exemplary procedures that may be applied to shorten the training time for some patterns.

One type of pattern is a pattern that includes parameteric input, for example feedback, and generates different outputs depending on the parameteric input. In an exemplary embodiment of the invention, such a pattern is trained by training multiple patterns, each with a different set of values of the parameteric input. Alternatively, system 400 detects the actual input pattern and varies the expected output signal based on the input pattern. Such varying can be useful, for example, for taking into account sensory input. For example, a position of a leg may be provided by a sensor to processor 410 and via kinesthetic sensory paths to the motor region determining a leg flexion.

Another type of pattern is a pattern with multiple intermediate steps, for example, a sequential motor program, such as writing a letter. Optionally, the program is trained as a whole, for example, repeating the input until a program to write the letter is generated from existing subprograms. Alternatively, the pattern may be trained step by step, for example, first training the first stroke and then using the output signal of the first stroke as one of the input signals for training the second stroke, Another type of pattern is a pattern with multiple intermediate parts, for example, a pattern involving multiple brain areas. One example of such a pattern is kicking a ball, which includes seeing the ball, aiming the leg and flexing the leg. Each of these actions use different brain area. In an exemplary embodiment of the invention, the training in each brain area is performed separately. Once the training of one area is completed, the next area may be trained. Alternatively, they are trained in parallel. Once all the areas are trained, a unified training session covering all areas may be performed. Alternatively or additionally, the interfaces between the brain areas are trained.

In an exemplary embodiment of the invention, pairing is to link together two parts of training. In pairing, the two areas to be paired are stimulated together (e.g., using a physical or other method of stimulation). Optionally, periodically a testing of the pairing is performed, by stimulating only one area (e.g., a source areas) and determining if the target area responded. If so, a rest period is optionally initiated. Optionally, pairing is enhanced by selectively controlling a general stimulation signal in accordance with the above described training method. Pairing maybe used, for example, to link the activation of large groups of neurons (e.g., low-resolution pairing), to link individual neurons or small groups of neurons (e.g., high-resolution pairing) and/or to link different brain areas, for example, a sensory region and a motor region.

Another type of pattern is one in which normally unconnected brain areas, e.g., far apart areas in different compartments of the brain, are to be linked. For example, control of the vagus nerve leading to the pancreas is generally not linked to motor areas. In an exemplary embodiment of the invention, such linking is achieved by making multiple small steps between areas that are better linked, so that the training time will be relatively short. In a pancreatic example, the linking means that a certain motor command, under conscious control, for example, will increase or reduce insulin generation.

Another type of pattern is one in which the output has a large range of possibilities, for example, moving a hand to a position in space, but is formed of hierarchical or linear component parts. In an exemplary embodiment of the invention, the training is performed for component parts of the motion, e.g., 10 different positions of the shoulder, 10 different positions of the elbow and 10 different positions of the wrist. Together, these component parts can be assembled into over 1000 different hand positions. In an exemplary embodiment of the invention, the composing of these component parts into a coherent whole is "discovered" by the brain, after the direct training. Optionally, such discovering is assisted by a suitable set of physical or mental exercises, for example a set of positioning tasks.

Another possible method of training a pattern is using scaffolding, as described above, in which certain exemplary patterns are trained and the user learns various on his own, or at later training sessions.

User Awareness Level

In some embodiments of the invention, user participation and/or user awareness are not required as part of training process. In an exemplary embodiment of the invention, a user is trained while he is asleep. A potential benefit of sleep training is that actual motor commands to the limbs are naturally blocked from being sent to the body during part of the sleep period. Alternatively or additionally, the user is placed under sedation. Alternatively or additionally, motor axons exiting the brain may be blocked for part of the training session, for example using electrical or chemical methods.

However, in an exemplary embodiment of the invention, the user being aware assists the training process, for example, by actively searching for newly implanted training (e.g., for connecting components of training) and/or connecting together training components. Alternatively or additionally, the user may be used to test the training, during the training session. Alternatively or additionally, the user provides "normal" brain patterns for triggering or for mapping, for example patterns that mean "move arm up". Alternatively or additionally, the user provides feedback that a desired output signal was achieved. Alternatively or additionally, the user provides feedback on the success of or the process of the training, for example for cognitively related training.

In an exemplary embodiment of the invention, the training methods described herein are combined with bio-feedback, for example, biofeedback methods serving as a scaffold and/or to fill-in a scaffold training provided by the present invention. Alternatively or additionally, user participation, focus and/or control of the body may be enhanced using hypnosis.

In an exemplary embodiment of the invention, however, the motivation of the user does not directly affect the learning process. Thus, it is useful for training of animals or people with motivation problems. This is possible in some embodiments of the invention, since the feedback and modification of learning and retention is provided by an external mechanism, rather than by a user's participation.

Following is a definition of learning taken from "http://pespmc1.vub.ac.be/ASC/LEARNING.html", a dictionary of cybernetics:

"A process of growing success in a fixed environment. E.g., mastering the violin, acquiring linguistic skills, increasing the accuracy of guesses, driving safer (Ackoff). Thus learning is not the same as acquiring knowledge through reception of information even though this often precedes manifest improvements. Learning is also different from problem solving which involves making decisions of how to bridge the gap between a present and a desired state and adaptation which implies changes in response to a changing environment not necessarily of growing success. One can only speak about learning when behavior noticeably increases the efficiency with which information is processed so that desirable states are reached, errors are avoided, or a portion of the world is controlled. Consciousness may or may not be involved. Learning by trial and error is a process by which feedback on errors prevents unsuccessful behavior from reoccurring thus increasing success. (Krippendorff)"

In an exemplary embodiment of the invention, this degree of learning can be achieved using the methods of the present invention, not only without consciousness, but also without motivation and/or provision of feedback via normal channels. Furthermore, in some embodiments of the invention, no reward or punishment of any type is provided on any level.

Training Automation

In an exemplary embodiment of the invention, training is applied as a one or more pre-defined sessions. Such a session can include, for example, a set of input signals, a set of desired output signals, a number of times to repeat training and/or thresholds of the quality of matching the desired output. In addition, a training protocol may include other elements, for example, rest periods and mental exercises.

Optionally, the number of sessions or the content of the sessions is changed by an operator, for example, in response to the progression of the training. Such modification may be between sessions or within sessions.

Optionally, the user serves as his own operator, for example setting the training session sequence and/or parameters.

Optionally, a semi-automated or automatic monitoring mechanism is provided. For example, a user can set a goal and the mechanism will attempt different training protocols until the goal is met or some time period or other limitation is met. In an exemplary embodiment of the invention, an automatic mechanism is used to enforce rest periods, rather than relaying on a user's judgment.

Unlearning and Extinction

In some situations it is desirable to unlearn patterns in the brain. In an exemplary embodiment of the invention, unlearning is achieved by stopping a "training" process at a plurality of points, at each of which points the output signal is different. In one example, unlearning is used for deleting previously imposed patterns that are not desired any more. It should be noted, however, that in some cases and parts of the brain, unused patterns will decay on their own.

Alternatively to destroying a pattern, in an exemplary embodiment of the invention, a pattern may be retrained. For retraining, the input signal is identified and excitation is stopped when the output signals approaches the new desired output signal. At the beginning of the process, deviations from the previous output, towards the desired output may be small, due to the trained nature of the pattern. In one example, a pattern for moving a right arm is over-written to generate output signals to move the left arm. In another example, a pain sensing area is overwritten and reduced in size, to reduce a sensation of pain.

Search Range

As noted above, one property of neural networks that may assist training is exploration. When an input is provided to a network, the network searches through a wide variety of neuron connections to generate a range of patterns. Selectively enhancing certain activation patterns comprises training, in some embodiments of the invention.

In the brain, far-reaching searching allows two different brain areas to be linked together by training. In some cases, however, such linking may not be desired. instead, it may be desired to limit training to a certain brain area, for example, for safety reasons.

It should be noted that the brain is naturally (and/or as a result of life-long training) compartmentalized and linked, so that some degree of order is imposed on the search. For example, the sensory and motor areas are naturally linked, while the auditory and kinesthetic areas are generally less so linked. Alternatively or additionally, the search may be limited to a brain region by blocking impulses out of the region. Such blocking may be achieved, for example, using an electric field to hyper-polarized neurons in a boundary surrounding the region or areas in which training is undesired, or by using chemical substances that block neuronal activity.

Alternatively, blocking is indirectly achieved by selectively exciting one part of the brain, for example using chemical or electrical means, so that that part will be more receptive to training and changing connections. Thus, other parts of the brain will be less likely to partake in actual training, even if they may be activated by the training process.

Alternatively or additionally, in an exemplary embodiment of the invention, spatially selective general stimulation may be selectively applied only to those areas in which training is desired.

In some case, as noted above with reference to broken-down training, it may be desirable to create links between brain areas, possibly prior to performing to total training. For example, a link may be created (e.g., using pairing) between an auditory processing area and a kinesthetic processing area, to assist the exploration of a later training session in bridging the distance between the areas.

Optionally, a plurality of training sessions are applied in parallel, to different parts of the brain. The neurons activated by the parallel training sessions may be more likely to link together. Alternatively, neurons, that it is desired to affect by training, may be directly excited even without an orderly training process.

General Stimulation Based Training

As noted above, in some embodiments of the invention, the training is achieved by stopping a general stimulation when a desired output is generated, alternatively or additionally to stopping an input signal. A potential advantage of this type of training is that general stimulation is easier to achieve from outside the brain using physical and/or other means, as described above. Sensitive sensors or the user's reporting may be used to detect that a desired output was generated. Thus, in some embodiments of the invention, no invasive electrodes are required.

In an exemplary embodiment of the invention, general stimulation is used as part of a pairing-type training, for example, providing a general stimulation while pricking a user in the hand and instructing the user to think of the letter "A". Feedback that the pairing is achieved, may be provided for example, by pricking the user without warning (e.g., so he is not thinking of "A" or during a time when the user is instructed to think of the letter "B") to see if the thought about the letter "A" was activated. If it was, a rest period is optionally initiated (where the general stimulation and/or input signal are stopped, reduced and/or changed, e.g., as part of a different trained pattern)

Preventing Destabilization

A potential problem when modifying the brain's activity is that of destabilization of brain function. Such destabilization can be, for example, at the organizational level, in that the brain cannot keep a focus. Alternatively or additionally, the destabilization on at a signal level, in that chaotic signals, possibly seizure causing, are created.

In an exemplary embodiment of the invention, such destabilization is avoided by limiting training to well-defined regions of the brain. For example, higher level areas (e.g., frontal lobes) or areas dealing with relatively autonomous body functions maybe avoided or intentionally blocked, at least in some embodiments.

Alternatively or additionally, an inhibiting training pattern may be trained that inhibits output signals from a brain area if certain fault conditions, such as over stimulation, are discovered by the pattern. Alternatively or additionally, such inhibiting patterns are trained on a brain-wide scale, independent of which regions were trained. As will be described below, such a damping mechanism may also be useful for treating epilepsy.

Alternatively or additionally, an electronic pacemaker is provided for artificially stopping the propagating of excitations and/or treating seizures.

Alternatively or additionally, destabilization is prevented by planning the trained patterns so that they do not have a negative, destabilizing interaction with each other and/or the brain.

Alternatively or additionally, destabilization is prevented by testing for warning signs (e.g., unusual EEG variations) during training and/or between sessions. In an exemplary embodiment of the invention, mental exercises simulating potentially destabilizing conditions are performed, to attempt to force destabilization. An exemplary such exercise is one that requires divided attention and/or is at a limit of the user's ability. A reduction in ability may also indicate a potentially undesirable side-effect.

Alternatively or additionally, destabilization is prevented by spreading out training sessions over a long period of time so that only one component is trained at a time. The intervening time is optionally used to check for adverse effects of the training, including destabilization.

Alternatively or additionally, training is applied first as a skeleton of basic, partly learned patterns, on which destabilization tests are performed and then the training is made more complete.

Combating Side Effects

Training of new patterns may cause side effects that are less than destabilization of the brain. For example, training of a new hand motion, may cause the hand motion to be generated when inappropriate, or it may cause a second hand motion to be generated as well.

In an exemplary embodiment of the invention, such side-effects are detected after training and specific training and/or exercising is applied to prevent or overcome the side effects. In one example, the user is exercised in performing only the new hand motion and to suppress the second hand motion. In another example, the user is trained not only in activating the new hand motion, but also in suppressing it, even when the correct triggering signal is provided.

Alternatively, various sedatives or other psycho-active drugs may be used to combat side effects.

Exemplary Applications

As can be appreciated, the range of possibilities in training the brain is similar to that of training a general purpose computer, e.g., substantially infinite. Following, however, are a plurality of exemplary applications of training neural networks in the body. It should be noted that some of the applications use hardware only during a training stage, while other applications use hardware also during the usage state. In particular it should be noted that some applications assist in interfacing hardware to the body, other applications use hardware in order to operate, while still other applications only require hardware for a setting up the application. Some applications may be trained using only a previously trained pattern, and using no direct neuron-interfacing hardware.

Ambulatory Training Device

Setup 400 may be provided as a laboratory device. Which is not generally portable with a user. Typically, portable devices (excepting implanted devices) have a lower resolution and processing ability than stationary devices. In an exemplary embodiment of the invention, a stationary setup is used for imposing the training, while an ambulatory device is used for follow up. In an exemplary embodiment of the invention, the ambulatory device is worn on the waist and is connected to electrodes and/or sensors by wired and/or wireless means.

In an exemplary embodiment of the invention, the ambulatory device is used to monitor the success of training and/or record brain activity (possibly generated by the trained pattern for this purpose). Alternatively or additionally, the ambulatory device is used to modulate the training. For example, the ambulatory device may apply general stimulation while the trained pattern is being used in a desired or undesired manner, while the basic training is applied using a stationary device. Alternatively or additionally, the stationary setup is used to prepare input areas for the ambulatory device. Optionally, the ambulatory device includes means for communicating with the user, for example, a keyboard or a visual or auditory display, so that the user can report to the device and/or receive instructions from the device.

Alternatively or additionally, the ambulatory device assist in completing training. For example, in an application when two areas are linked together, the ambulatory device can read from one area and write to a second area, before the brain is sufficiently trained to perform the linkage. Alternatively or additionally, the ambulatory device is used for performing processing not currently performed by the trained parts of the brain, for example, if a particular training session is not yet performed.

Alternatively or additionally, the ambulatory device is used for other applications, as described below. Additional, optional, technical details are provided below.

Motor Control

Figure 6:
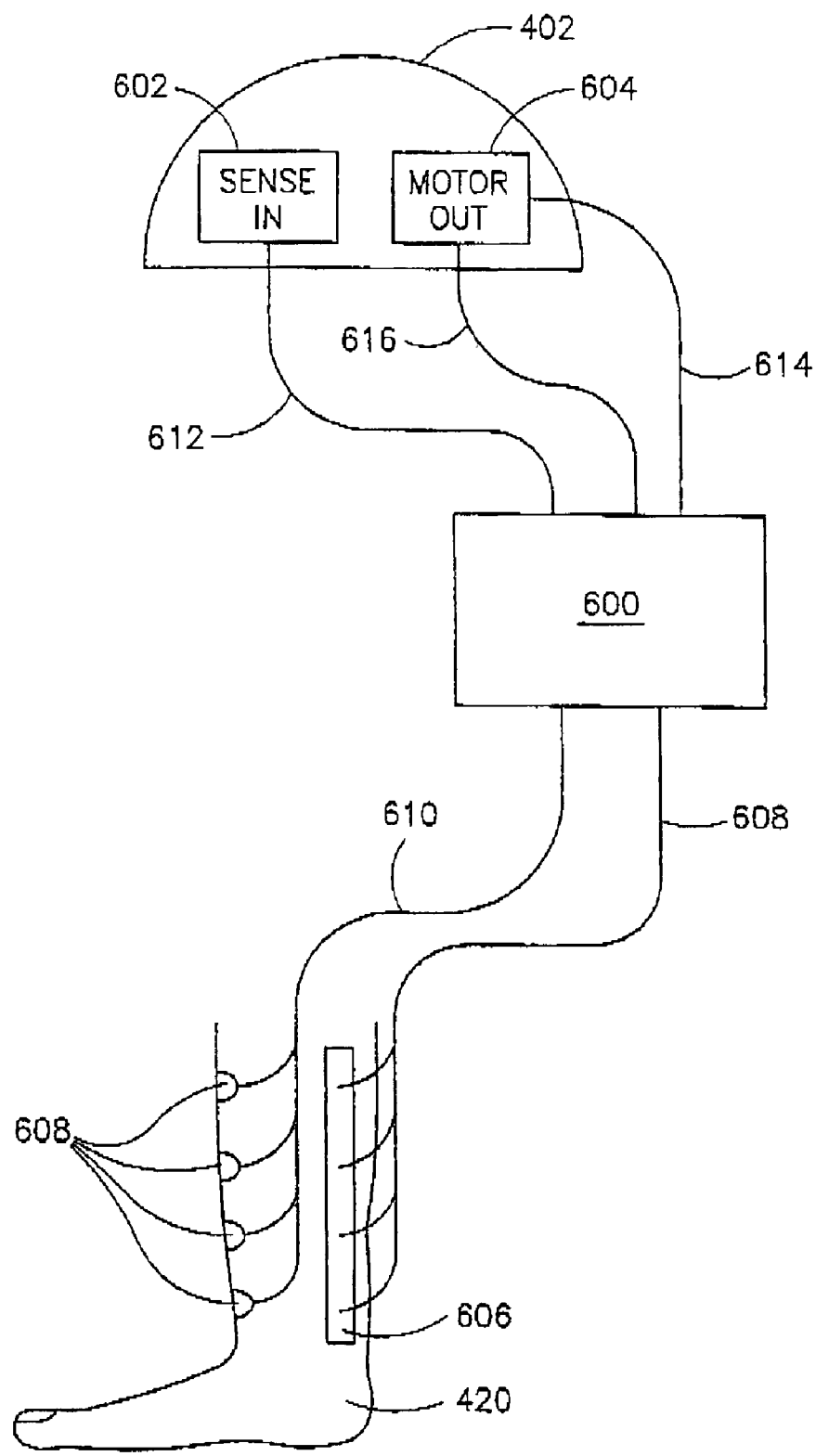
FIG. 6 illustrates a limb activation device for use in connecting a brain to an appendage, in accordance with an exemplary embodiment of the invention.

FIG. 6 illustrates a limb activation device 600 for use in connecting a brain 402 to an appendage 420, in accordance with an exemplary embodiment of the invention. Appendage 420, which may be paralyzed (e.g., nerve block) or artificial (e.g., no nerves) is interfaced to brain 402, so that it can be used. A benefit, which is realized in some embodiments of the invention, of using the brain as a command source, is that the brain commands all the body, so that commands to the appendage and to other parts of the body can be naturally synchronized. In addition, the brain is uniquely designed to processes sensory input, provide motor commands and learn from experience. In addition, many useful motor patterns are already programmed into the brain. It should be noted that the previously trained motor patterns may be useful also for unnatural appendages. For example, eye-movements may be usefully used for controlling a CCD camera.

Theoretically, a paralyzed limb could be reconnected to the brain, by electrically attaching the axons exiting the motor area to the nerve endings at the limb. However, this requires providing long-lasting electrical connections to a multiplicity of axons, which appears to be beyond current technology. In addition, unused parts of the brain may have been taken over by other functions and need to be recaptured for the use of the paralyzed limb (this may be provided for however, by some embodiments of the invention). An alternative solution is recognizing motor patterns by detecting neuronal activity using an array of electrodes. Typically however, such an array lacks the required resolution and/or is heavy and/or expensive. In addition, the opposite task, of connecting sensory signals from the limb back into the brain, cannot be satisfactorily performed using current prior art techniques.

In an exemplary embodiment of the invention, one effect of training the brain is to increase the discernability of output signals in the motor region, so that they can be better detected (e.g., better resolution and/or using a lighter device). In an exemplary embodiment of the invention, the discernability is increased by increasing the size of the output area. Alternatively or additionally, the discernability is increased by increasing the organization of the signals. For example, the output signals can be mapped into an array or large signaling areas, which are easy to detect and differentiate using relatively simple technology.

Alternatively or additionally, training is used to impose at least basic patterns that relate current (or create new) motor programs and the enervation and/or to relate (or create new) sensory analysis ability and the new input.

In an exemplary embodiment of the invention, relating is used to teach a brain at least a rudiment of the control of an artificial limb that uses non-muscle actuators and/or non-nerve sensors (or, a regular limb with artificial connections thereto). Optionally, device 600 maps between brain signals and motor commands to an artificial limb (or a microprocessor on a limb may do such performing). For example, 20 output areas in the brain, each with 10 output levels may be mapped onto 10 different control parameters, each with 256 levels, of the limb. The mapping may be selected, for example, based on a user indication of what movement was meant. Alternatively, at the start, a random mapping is used. In some embodiments of the invention, the mapping is selected so that the number of different detectable patterns is larger than those that can be used by the limb, for example, being 2, 5, 10 times as much. In an exemplary embodiment of the invention, the hardware of the limb is programmed with a precise mapping, however, the brain is left to its own devices to determine the details of most of the mappings.

Alternatively or additionally, training is used to impose new motor loops, for example, blocking input from a sensory neuron when a desired motor output is generated.

In an exemplary embodiment of the invention, device 600 provides electrical stimulation via a plurality of signal lines 608 to a muscle 606 (in a real limb) or an actuator (in an artificial limb). An advantage of using existing nerves is that they are well distributed in the limb. A disadvantage of real nerves is the difficulty to connect to them. Optionally, the motor nerves in appendage 420 are indirectly stimulated (or muscle 606 stimulated) using external electrical stimulation. The "instructions" for simulation are provided via a line 614 from a motor region 604. It should be noted, that in accordance with some exemplary embodiments of the invention, device 600 merely reads the motor region and passes the readings to the nerves, possibly providing amplification. Any processing is performed by the brain. Optionally, device 600 is used to emulate processing capabilities not yet trained into the brain. For example, in the above CCD camera device, the movements may be controlled by the visual cortex, possibly in response to images acquired by the camera. However, zooming-in control of the camera may be provided by device 600.

Sensory signals from real nerves or artificial sensors 608 are optional provided via signal lines 610, through device 600, to a cable 612 connected to a sensory region 602. Alternatively or additionally, brain 402 uses feedback from the balance sense and/or the visual sense of the person. Alternatively to connection to the sensory area, the connection of the nerve output can be directly to motor area 604.

In an exemplary embodiment of the invention, training includes only providing a scaffold of movements sufficient for the user to start using the limb and learning more exact movements himself. This learning may cause remapping of brain function.

Optionally, various spinal functions such as reflexes, are trained into motor area 604.

It should be appreciated that motor training may be useful also for implanted limbs, for which the mapping to the user's brain is generally incompatible with the previous mapping (even if not yet degraded).

In an exemplary embodiment of the invention, where the damage is along the tracks from the brain along the spine the activation is at the Motor Cortex 1 and around the damaged region. Sensing may be peripheral only.

In an exemplary embodiment of the invention, for motoric rehabilitation, the motivation of activating a specific muscle or organ can be either conscious or unconscious. It may be preferable to ask the patient to perform the task, thus inducing some amount of activity to be enhanced (e.g., so method provides improvement from low level to high level rather than from zero to something).

An exemplary stimulus location is SMA (supplementary Motor Area). In the case of tumor, aneurysm, stroke or trauma possibly surrounding the damaged region as well. Stimulation of Motor cortex 1 may or may not be necessary. Measurement (e.g., output) may be provided, for example, using EMG on selected muscles, evoked potential along peripheral nerves, and/or EEG.

In an exemplary embodiment of the invention, the patient is first shown the operation of the method by training an operational organ. In one example, the patient holds a paper between his two fingers. This induces a low level of EMG. By applying the above training process, with stimulation of the SMA, unconscious modulation of the EMG signal is produced, for example, by changing the overall level of contraction, or by changing the time distribution of the EMG signals. Optionally, this is linked to a rhythm (e.g., of music). The patient can then see that the method works and is harmless. At the same time, various parameters (such as desired rest period and stimulation strength) can be determined.

One exemplary training sequence is based on time dependent Hebbian learning. A patient is presented with a series of stimuli (either auditory or visual). One of the stimuli will be repetitively paired with magnetic stimulation of the primary motor cortex, inducing muscle contraction. EMG ill be recorded from the muscle in order to detect motor response even when it is not detectable visually or by the patient. EEG is also optionally recorded, for example, to evaluate the influence of TMS on the brain and monitor the changes in neural activity resulting from learning. As a more advanced test, associations can be created in which either a 'trigger' or response or both are neural activities with little or no external expression. Such associations are useful, for example, for sensory training, below or for rehabilitation.

Sensory Training

In an exemplary embodiment of the invention, training is used to provide sensory enhancement (e.g., relative to a baseline, for example by changing relative sensitivity to different stimuli or increasing sensitivity, or to provide rehabilitation for damaged sensing abilities (e.g., stroke, peripheral damage).

In an exemplary embodiment of the invention, the measurement of output is by standard threshold (or other) tests, for example, auditory system threshold: for each frequency playing several levels (e.g. 5), some below threshold and some above, testing the number of 'hits', and changes in the hit/miss ratio.

A possible criteria for removing the stimulus is every hit, or every improvement of hit/miss ratio (within some window, say 5 events).

In the example of the eye, detection threshold of visual signals (dots, lines, shapes, color dependent, orientation dependent).

In all these threshold tests it is possible to include low background noise, tones or patterns, for example, in order to exclude effects of concentration, and providing a reference.

The location of stimulation is optionally directly to the cortical region related to the sensor.

Other examples are provided below with relation to rehabilitation.

Cognitive Teaching

Alternatively, general stimulation and stopping stimulation of the brain (or parts thereof) may be used as an adjunct to teaching a complex task and/or abstract ideas. For example, stimulation is stopped and/or rest is provided, when an abstract teaching is correctly applied. Optionally, the task is subdivided, so that a rest/stop may be provided after every part of the task.

A different type of cognitive teaching is modulating cognitive abilities, for example, improvement of attention concentration and/or memory (e.g., for learning disorders, 'deselection', autism)

Example of tests are: reading speed, speech discrimination, writing (spelling), right-left discrimination, repeating a sequence of items (short term memory).

Example of method: stimulation where the performance is low, removal when improved. Stimulation during provision of exercises in which problematic abilities are expected to take part.

Example of location: Globally to the frontal cortex or to improperly functioning areas.

Examples of stimulation method: TMS and/or implantable electrode(s).

Input/Output Interface

Figure 7:
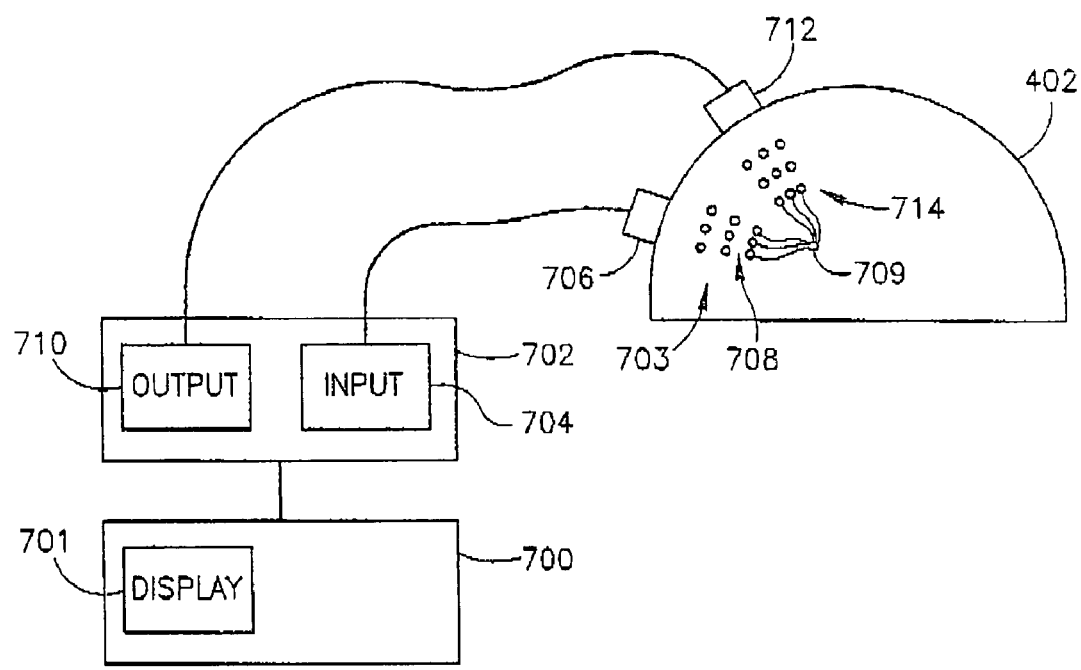
FIG. 7 is a schematic illustration of the connection of a computer to a brain, using an I/O interface, in accordance with an exemplary embodiment of the invention.

FIG. 7 is a schematic illustration of the connection of a computer (or other device) 700 to brain 402, using an I/O interface 702, in accordance with an exemplary embodiment of the invention.

One problem with interfacing a computer or any other device to the brain is the need to selectively excite and/or read certain neurons, in a meaningful manner, so that the computer can bypass the natural input output means (with relatively low serial bandwidth) that the human body is naturally provided with. In addition, these natural i/o means typically require a user's attention, which further limits the effective bandwidth.

In an exemplary embodiment of the invention, a neural interface 703 is constructed in the brain, by training the brain. In an exemplary embodiment of the invention, I/O interface 702 includes an input component 704 that stimulates the brain neural signals in an input area 708 of neural interface 703 using a stimulator 706. The signals pass through neuronal pathways to an area 709 (or multiple or distributed areas) that process the information, either naturally or using methods that were trained in. The output is conveyed from area 709 to an output area 714 of the brain, where output signals are read by a detector 712 that is coupled to an output potion 710 of I/O interface 702. Optionally, information is displayed on computer 700, for example, using a built in display 701, for example, input from the brain or data to supplement what is provided directly to the brain. Alternatively or additionally, an input means may be provided in computer 700.

A simpler I/O interface may include only input or only output, for example, only an input pathway to provide a time of day coordinates to a visual cortex part of the brain, where the input signal is converted into a clock hands position. Alternatively, only output pathways are provided, for example, to expose motor programs for forming words, as part of a speech detection system.

Optionally, computer 700 or at least interface 702 are implanted.

In some embodiments, only input or only output (e.g., commands from the brain) is provided. Although wireless stimulation and detection means are shown in the figure, in some embodiments of the invention, the means include implanted electrodes.

In the exemplary embodiment shown in the figure, the access areas are depicted as an array of individually accessible points in the brain. This array is trained to selectively stimulate neurons in area 709. Optionally, the array itself comprises the function of area 709. Alternatively or additionally, the same array are used for input and output. Alternatively, a separate area (not shown) is trained for converting the input signals into neuron addressing signals In an exemplary embodiment of the invention, the interface formed of neural tissue provides one or more of the following functions:

a) Defining i/o areas where brain tissue is more accessible, less sensitive and/or more amenable to training. For example, these areas may be naturally linked to accessible sensory inputs or motor outputs or they may lie closer to the brain surface.

b) Matching the size resolution of the technological means (e.g., low resolution) to the resolution of brain areas that are accessed. For example, a 1 mm$^3$ access area may be used to selectively stimulate a well-defined visual receptive field in the visual cortex. For example, the access area may be paired to the neurons by stimulating both the area and the neuron (e.g., using a visual field stimulus) at a same time. In an exemplary embodiment of the invention, the various patterns possible in the input area are converted into an address for the particular neuron to be excited, for example, by training a group of neurons to receive as input one of the various patterns and generate as output a signal which will selectively excite the neurons to which the input is intended.

c) Matching the gray level resolution between the input and the stimulation of the neurons.

d) Improving distinguishability, by forcing the different datum to be separable in the input and/or output, by suitable spatial and/or temporal coding.

e) Format conversion, between computer 700 and brain 402, for example, converting gray-level data into frequency signals.

f) Buffering and data latching, for example, to match transmission speeds of I/O interface 702 to the relatively slow processing rate of the brain, for example by converting serial input into parallel input (and likewise with output). Such buffering may also be useful for matching synchronous activity of computer 700 and asynchronous activity of the brain, in which different processing cycles may have a different duration. Possibly, such a buffer is implemented by training a brain area to repeat its input after a delay and/or to maintain an output for a while. An exemplary 50 msec latch is described in the experimental section below (e.g., if the incoming and outgoing signals are the same)

g) On demand I/O. For example, interface 703 receives input or provides output when stimulated to do so by interface 702, and not continuously. Output area 714 optional includes a section that indicates when output is ready, for example by generating a suitable output signal. Other handshaking protocols may be implemented as well.

h) Provide a parallel command channel for the user to provide or receive commands that bypasses various psychophysical input and output channel difficulties, such as noise and low bandwidth. In an exemplary embodiment of the invention, the brain itself serves as a translator between internal states and intentions and signals that can be better distinguished by a computer.

Possibly, at least some of the above functions, for example data conversion, are performed by I/O interface 702.

It should be appreciated that the training described herein may be applied to any age of subject. In particular, it may be desirable to prepare infants for a later implantation of a neural interface by creating or reserving parts in the brain for input and output. Such reserving and training may include defining groups of neurons that act together and ensuring that the neurons are well connected to various parts of the brain.

Bypass Interface

Figure 8:
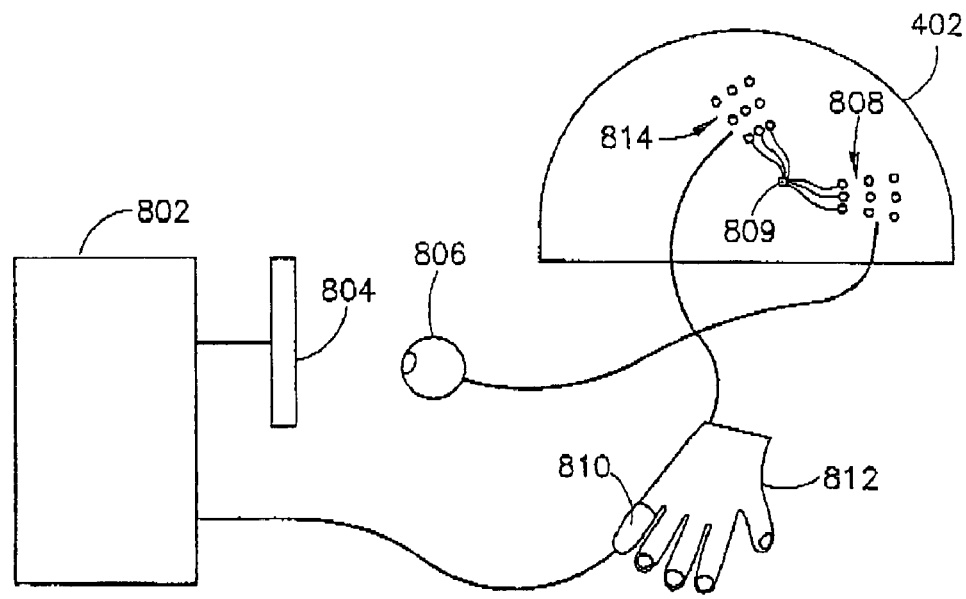
FIG. 8 is a schematic diagram of the connection of brain areas, in which the natural i/o means of the body are used to provide input or output to the brain, in accordance with an exemplary embodiment of the invention.

FIG. 8 is a schematic diagram of the connection of brain areas, in which the natural i/o means of the body are used to provide input or output to or from brain 402, especially a trained section thereof, in accordance with an exemplary embodiment of the invention. Optionally, however, the provision is unconscious in that there is no or a reduced amount of conscious attention to the input and output. In one example, a display 804, of an I/O interface 802 displays images to an eye 806, which, after processing in the brain's visual cortex, stimulate an input array 808. The stimulation passes to a processing area 809, and output is provided to an array 814. The output from array 814 passes through a motor cortex to activate, for example, a hand 812 (e.g., cause muscles in a finger to tense and relax), where the activation is detected by a sensor 810.

In an exemplary embodiment of the invention, special codes and/or patterns are used on the input, so that everyday activities will not cause inadvertent activation of area 809. Alternatively, the user is trained or exercised in repressing the recognition of the input patterns.

In an exemplary embodiment of the invention, once training is completed, no direct interfacing with neurons is required.

Although training can be used to directly connect a visual input to a particular motor output, this is a complex training and may not always be desirable. Instead, "standard" input and/or output areas are defined, which are possibly capable of being monitored or written to using external equipment. Thus, the actual linking of an input to a sensory modality or an output to a motor modality, may be avoided.

Exemplary Device Configurations

FIG. 4 shows a generalized device. As noted, this device may be used for training and/or for keeping up training. In an exemplary embodiment of the invention, a modification of this device is used for interaction with a brain, after the brain is trained. This modified device may use a smaller or no general stimulator and optionally use existing inputs (e.g. senses) to provide input to the brain. For example, this device may include one or more input and one or more output electrodes, connected to a suitable controller. A connection to the outside world may be provided, if required. In an exemplary embodiment of the invention, the device is implanted. Alternatively, it may be worn and/or may comprise an implanted stimulator, an implanted detector and/or an external controller and power supply. Transmission of power and data between the components may use methods well known in the art, for example magnetic interfaces, with coils implanted under the skin of the skull.

In an exemplary embodiment of the invention, TMS is used to induce specific long-term changes in cortical connectivity according to pre-defined criteria. In an exemplary embodiment of the invention, the device includes a closed loop TMS system which will continuously monitor cortical functioning via EEG recording and modify it using TMS.

Brain as I/O Interface

Alternatively or additionally to using the brain as a processor to which information (e.g. limb position) is provided and/or processed data received (e.g. motor instructions), the brain may be used as an I/O system for the user. For example, providing output to the user by making the user sense the output or providing input from the user, for example by recognizing the user's speech intentions, rather than detecting speech.

The general setup may be similar to that shown in FIG. 7 or in FIG. 8. In an exemplary embodiment of the invention, a mind display is created by associating patterns in different areas of the visual field with various stimulation signals from area 703. For example, a user may be trained to associate pin-pricks with letters. A message may then be provided to the user using a series of pin-pricks.

In a similar manner, commands from the user may be detected, for example, by associating different output patterns of area 714 with different speech sounds.

In the example of FIG. 8, simple visual patterns may be translated (e.g., by mapping) into high resolution visual effects, for example, allowing a virtual reality display to be enhanced by the user's active imagination or even created from a simple visual or tactile input. While enhancement of an input may be inherent in the sensory behavior of people, the training may be used, for example, to strengthen the enhancement and/or to define a desired enhancement, for example, promoting uniformity between people. In an exemplary embodiment of the invention, such training, for example of an airplane image, is provided by training a user with a plurality of detailed images relating to the airplane image and linking the high-resolution training images with lower resolution inputs.

In an exemplary embodiment of the invention, the use of the brain as an I/O interface provides one or more of the following functions:

a) Provide an additional high-bandwidth, low attention channel for input to the user (e.g., instead of an additional screen) or commands (e.g., instead of a keyboard) from the user, which, optionally, do not compete with the attention required by visual tasks and/or motor tasks.

b) Convert inputs into conceptual displays.

c) Create tactile output signals (e.g., pain or tingling in a body portion). In one example, a user is told to think of an object or idea, for example the letter "A" and simultaneously pricked in his arm, until the user feels the pricking as a response to identifying the letter "A", even without active pricking.

d) Convert between sensory modalities. For example, using visual signals to recreate both visual and kinesthetic sensory fields.

e) Create motor output. In an exemplary embodiment of the invention, the training links input to the user or output for the user to motor programs, such as typing and enumerating.

Adding Circuits

In an exemplary embodiment of the invention, the above training methods are used to impose logic processing on the brain. A potential advantage of logic processing is that it is more easily debugged and understood. Another potential advantage is that its basic operation may interfere less with brain activity, as its function is foreign to regular brain activity.

In an exemplary embodiment of the invention, an array of electrodes (e.g., 100 electrodes) is inserted into the brain, so that each electrodes reads and/or writes a small number of neurons, or possibly only a single neuron.

Groups of electrodes may be selected to train the corresponding neurons to respond as a logic gate, for example, "AND" or "NAND". Possibly, different electrodes may be more suitable for different logic gates. For example, if the electrodes capture inhibitory neurons (or neurons that excite inhibitory neurons), a "NAND" gate may be easier to achieve. Thus, some electrodes/neurons may be rejected in general or selected for certain types of gates. Linking of gates may be achieved, for example using the pairing mechanism and/or training as described above. The gates may be trained/imposed in parallel or in series.

As well known in the field of electronic design, especially asynchronous design, a very wide range of useful circuits and processing elements may be constructed from individual logic gates. In addition, it should be noted that a neuron is a complex cell, so that certain functions, such as look-up tables, may be implemented as neural networks, with a small number of neurons, for example, as known in the art of artificial neural network design and programming.

The trained neurons may be linked with other parts of the brain and/or sensory or motor endings, for example using additional electrodes and/or other training techniques as described herein. In particular, the training may be used to amplify the output of a single trained neuron so that it affects a group of neurons or to collect signals from several neurons and direct them to a particular one of the trained neurons.

In an exemplary embodiment of the invention, a latch is trained into the brain, to retain data for a period of time and can serve as a memory device. Such a latch optionally includes an area trained to repeat its input to its output and then re-provide the output to the input, thus latching onto its input. A particular stimulation of the latch can be used to reset its memory. The basic components required for a digital computer can be provided, as well, thus allowing a digital computer to be built inside the brain, using neural networks as component pieces. Logic gates or more complex logic formulae, can be trained, for example, to emulate the desired truth tables. A comparator and a two-bit adder can also be trained by emulated a truth table. Another exemplary "logic component" is a clock, which generates a fixed signal independent of its input and which may include only a stop or start input. Such a component is trained to generate a continues output. While precise control of timing as possible in digital system may be impossible, the timing can be linked to an outside event or an outside clock.

It should be appreciated that while digital logic may be imposed, and may be simpler to implement due to its noise resistance, multi-level logic may be used instead, as a neural network is a multi-level element.

In an exemplary embodiment of the invention, a new circuit for adding numbers (or more complex arithmetic) is trained into the brain. The input can be, for example, the user visualizing two digits. The output can be, for example, a number floating in the visual field. The processing is, for example, by emulating a base-ten adder using a suitable logic formula, and one or more latches.

Other circuits may be added as well, not necessitating logic gates. In one example, a new reflex is added, for example, raising the left hand when a sudden bright light is shined. Another example, mentioned above, is the training of a finger to punch out a response code, to a challenge. Another example is translation of phonetic signals, form a computer output into auditory sounds, for example, for a speech input.

Epilepsy Treatment

Figure 9:
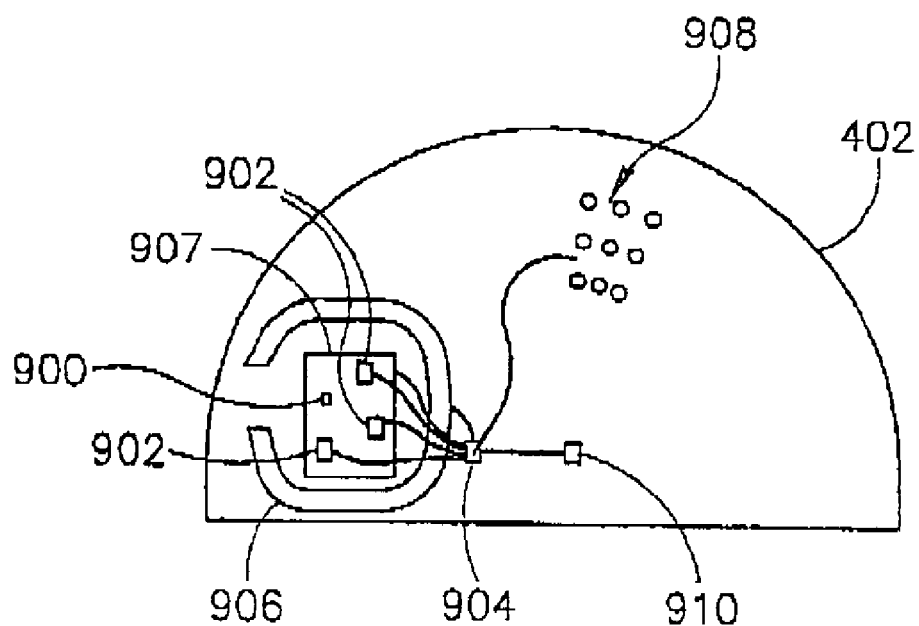
FIG. 9 shows a brain having a potential epileptic foci and training for preventing epileptic fits in accordance with an exemplary embodiment of the invention.

One example of a new circuit that can be added to a brain is for treating epilepsy. FIG. 9 shows brain 402 having a potential epileptic foci 900 and training for preventing epileptic fits in accordance with an exemplary embodiment of the invention. One or more brain area 902 are trained as sensors to detect is an unusual excitation is arriving. They send a signal to an epilepsy control area 904. In some embodiments of the invention, control area 904 is integral with sensing areas 902. Control area 904 then activates a damping ring section of the brain 906, that surrounds foci 900, and has the property that substantially all the cells in the area are prevented from propagating a signal and/or propagate at a reduces speed. Thus, the unusual excitation is stopped. Area 904 may be outside or inside ring 906. Alternatively or additionally to a ring, a damping volume 907 is activated. Alternatively or additionally, a spiral shaped (or otherwise convoluted) area is activated, so that pulses are forced to propagate a longer direction, thereby hitting a refractory time and stopping. Alternatively or additionally, an area may be "tired out" by repeated activation, so that its response behavior changes in a way that prevent an attack from propagating. It should be appreciated that in epilepsy many of the areas affected by training are large, so that training may not affect smaller scale operations. This may limit side effects of the treatment.

In an exemplary embodiment of the invention, TMS is used to find and stimulate an epilepsy foci. When such a foci responds, detected for example using high resolution EEG, ring 906 that should stop the propagation of the epileptic wave are stimulated, for example using TMS. Control area 904 (possibly with an unknown location) is created by the linking in the brain of the stimulation foci and the response of ring 906.

Alternatively or additionally to preventing propagation, an output signal may be provided by area 904, to an output area 908, for example, for a patient worn device, such as a medical telemetry device. Alternatively or additionally, the patient is alerted, for example, by a suitable excitation of his auditory area 910.

In an exemplary embodiment of the invention, self-induced damping, for example, by over stimulation of a brain area so that it requires "rest" in order to respond again fast, is used to inhibit foci of the brain that cause tremors, for example, in Parkinson's disease.

In treating epilepsy as well as in treating other neurological disorders (or enhancements) the use of drugs and stimulation or training may be combined. For example, one or more of the following interactions may be provided:

(a) training may be used to overcome a side effect of a drug and/or allow using a higher dosage or a toxic drug;

(b) one or more drugs may be used to overcome a side effect of the training and/or to assist in the training or in the operation of stimulation during an attack;

(c) training and drug may interact synergistically, with one enhancing the other;

(d) the application of drug and training may be temporally and/or spatially synchronized one to the other (possibly with a delay in time) and/or to a different event (e.g., an onset of an attack); and/or (e) both drug and training (per se or stimulation that uses a previously trained effect) may be provided as part of a multi-level therapy, with one or both and/or modifications thereof being applied depending on the type of attack, for example. Thus a treatment device may include a drug eluting element as well as a neuronal stimulation element.

Where available, an electrical stimulation regime may be used in addition to or instead of a drug for the above interactions.

New Brain Areas

New circuits and new functionality may be added to the brain by training parts of the brain that continue to carry out other functions. Alternatively, part of the brain may be selected to be used substantially only for the new function. The old function of the area may be lost or it may be moved to a different area. As well known from studies of cortical plasticity, motion, growth and/or shrinkage of functional areas are common occurrences. The new function may be centralized in a single area or it may be distributed between several areas. Optionally, the training is repeated periodically, to prevent the new area from being taken over by other functions. Optionally, the new area is blocked from nearby areas during training, for example using electrical or chemical hyper-polarization of a boundary, to reduce the linkage between the area and nearby areas alternatively, surgical sectioning techniques, for partial severing, may be applied.

In an exemplary embodiment of the invention, the new brain area is used for converting user thoughts into suitable output commands. For example, the new brain area is trained to command a prosthesis device and/or process input from a prosthesis sensory means. In one example, the brain and its motor axons are connected to a prosthetic device, such as an insulin pump or a pacemaker. Control and/or long term programming of a device may be a conscious effort. Alternatively, as described below, automatic control is provided, for example by feeding forward to the device input from the brain's own glucose sensors.

In another example, the new area is used for managing the treatment of epilepsy. In another example, the new area is used for managing input and output. In another example, the new area is used as a watchdog. Such a watchdog can, for example, detect destabilization of the brain, for example being trained to recognize a pattern of activation that indicates a seizure or unorganized activity and generate a response, such as a pin-prick sensation.

Optionally, the new area performs basic processing, for example, calculating the number of calories consumed, based on food identification and count per portion (e.g., using a lookup table). In another example, the new area is used for new functionality, such as interfacing with a prosthetic device.

The new area can be an unconscious area, in that the user is not aware of its activity (unless it activates other brain areas intentionally). Alternatively or additionally, the new area is consciously accessible, for example, the user being aware that the area is activated and being able to supply input and/or receive output from the area, at will.

Rehabilitation

In an exemplary embodiment of the invention, the above methods are used as part of a rehabilitation process, for example, for a stroke patient. In such a patient, one or more brain functions may be impaired or destroyed by the stroke, other brain functions may be intact, but limited in use due to lack of communication between different brain parts.

In an exemplary embodiment of the invention, the above methods are used in one or more of the following manners:

a) Program input and/or output areas, to allow an ambulatory apparatus to provide linking between brain areas and/or processing. The brain may be trained in parallel.

b) Create new brain areas or remap the missing functions to a new area, with at least a skeleton of the function required. The rehabilitation process may be used to fill-in and/or replace the skeleton.

c) Assist in creating linkage between brain areas, possibly, by training in relay areas in the brain, that forward signals from one area to another.

d) Combat phantom or real pain, by unlearning pain signals from the real or phantom organ.

e) Assist in coupling a prosthetic input and/or output device to the brain or couple a control pathway between the brain and a part of the body.

In some cases, the training above is used to supply that what traditional training and/or self-healing of the brain cannot supply (e.g., due to limited ability to interact with the brain for traditional treatment or lack of organized response in self-healing), for example, guidance of a rehabilitation process.

In an exemplary embodiment of the invention, standard rehabilitation is jump started and/or accelerated by imposing a training of a scaffold of the desired therapy. In one example, relearning the control of a limb in a high-level motor area damaged patient, maybe jump started by providing training for a small number of basic limb motions. The scaffolding is part of a process of remapping the control (that links the motor axons and the higher, undamaged, brain areas) to a functioning brain area. Once such scaffolding is in place, standard therapy methods can focus on relearning missing motor programs and control methods.

In another example, scaffolding is used to remap a part of the retina for a macular-degeneration patient. In such patients, part of the retina is unresponsive. However, it would be desirable to remap the functional part of the retina, in an organized manner, to make use of the part of the brain formerly used for the damaged retina portions. In an exemplary embodiment of the invention, such remapping is directed by training the user to respond with the unused part of the brain to signals from the undamaged part of the retina. In one example, the visual cortex is generally stimulated and the user is shown a flashing light in the undamaged part of the retina. The flashing and/or stimulation is stopped (for a rest) when the user reports that he has a sensation corresponding to the damaged part of the retina.

In another example, Menier's Disease, signals from the patient's vestibular system are reduced and/or amplified. Alternatively, part of the vestibular processing part of the brain may be overwritten by imposing a different, unrelated pattern on it. Alternatively or additionally, damping or remapping of functional brain areas may be useful in treating Tinitus and/or tetanus caused by physical damage. In such treatment, for example, an undamaged part of the brain is trained to take over the function of the damaged part.

Optionally, when a tumor is to be removed and an important brain area is located near the tumor, rehabilitation, (e.g., by remapping) is initiated before the tumor is removed, so that the immediate adverse effects of removing a functioning part of the brain, is reduced.

In an exemplary embodiment of the invention, remapping of sensory areas is used to more efficiently utilize available spinal cord channels in patient where a partial severing is in evidence (e.g., by an accident or a tumor). For example, utilizing linking circuits already in place in the spine, for example for reflexes and coordination, nerve ending for controlling the left side of the body may be used for controlling the right side of the body, possibly requiring the opposite side of the brain to do the controlling and training the limb to ignore what was previously a correct control signal.

Pain

When treating pain, it may be desirable to leave at least some residual pain, for at least some time, to prevent the user/patient form searching for pain.

In an exemplary embodiment of the invention, pain is treated by remapping a different function over the pain sensing area. This remapping may be active, for example, making it provide pain sensation to a different part of the body or it may be passive, for example, blocking signals from the pain source and allowing other functions to take over.

Alternatively or additionally, the remapping redirects pain signals to a part of the brain that does not deal with pain (e.g., a visual cortex). Alternatively or additionally, the remapping interferes with the network path of a pain signal, interfering with one of the many stations and paths that the signal takes from when entering the brain until felt by the patient as pain.

Alternatively or additionally, the pain sensation of the painful part of the body may be remapped to a new location (e.g., that of a different part of the body) in which automatic amplification of pain and/or connection to other brain center is reduced.

Alternatively or additionally, pain reduction is by untraining the pain sensing area, for example by starting and stopping stimulation randomly, whether or not pain is sensed. Alternatively, for example, the pain sending area is stimulated when there is no pain and the pain signal is artificially blocked when there is pain. In another example, the pain sensing area is trained to respond to high input signals, causing the response to low input signals typical of pain, to be overwritten.

In an exemplary embodiment of the invention, stimulation frequencies less than 1 Hz (e.g. 0.2-0.5 Hz) are used, for this and other applications, for two reasons: (a) safety—especially in TMS, but in general, to reduce probability of activation of epileptic episode (b) to prevent inactivation of the trained network by high frequency stimulation. This is based on a model that the response of a cortical network to a pulse has quite similar properties (duration of reverberating wave, recovery between successive pulses) as networks formed in a dish. Not all embodiments, of course, realize this model. Alternatively, the parameters of the model may be determined by empirical testing for a particular patient, type of stimulation and/or part of the brain.

In an exemplary embodiment of the invention, the following method is used for pain control:

A non-invasive stimulator (TMS—producing focused pulsed magnetic fields of up to 1-2 Tesla), is applied to various brain areas, for example, Contra-Lateral, Post-Rolandic and/or Pre-frontal areas. Exemplary amplitudes—around the threshold for 50% MEP (Motor evoked potential, for the brain as a whole or for the particular areas). Alternatively other amplitudes may be provided, for example, sub-threshold (e.g., 10%, 25%, 50%), supra-threshold (e.g., 110%, 150%) and/or any smaller, intermediate or larger value. Stimulation may be at one or more locations. The parameters may be different for different patients and may be maintained for a particular patient for a series of treatments and/or modified over time.

Treatment may include intentional induction of pain, using any method, in region from which the patient suffers and/or in a different region (e.g., for initial testing or setting up a baseline).

Possible measurement methods: report by the patient, measurement from EEG (e.g. P300 signal), Heart rate increase.

Criteria that when met the stimulus is removed/reduced)—reduction in pain perception level.

Invasive stimulus (and possibly recording as well)—with electrodes, needles (acupuncture) and/or implantable device may be used instead or in addition to TMS. Measurement can be, for example, as noted above for in-vivo drug testing.

Brain Organization

Figure 10:
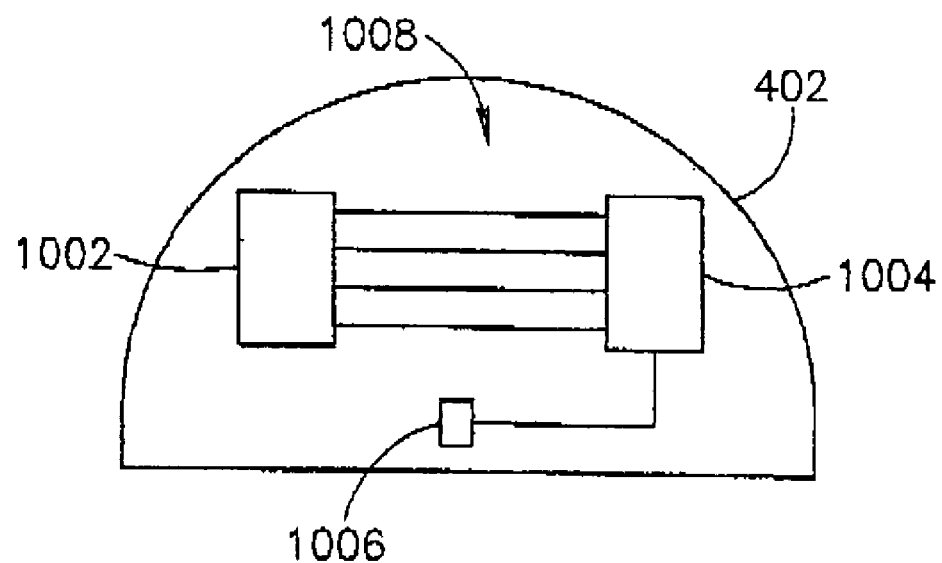
FIG. 10 illustrates an exemplary activation process in the brain.

FIG. 10 illustrates an exemplary activation process in the brain. A first area 1002 normally send signals to a second area 1004, over a plurality of paths 1008. It is expected that for communication between the two brain areas, such a multiplicity and disorder of paths is not necessary. Instead, a more limited path may serve just as well. In addition, it may be desirable to force the path to avoid a certain area, for example an area with exceptional sensitive to cross-talk or a damaged area (or a tumor area).

In an exemplary embodiment of the invention, the training comprises unlearning the other paths and/or imposing damping circuits that prevent propagation not along the desired path, by responding to signals along the paths by inhibiting neurons or groups of neuronal activity in the path. One potential advantage of such organization is less interference in the brain. Another potential advantage is that the communication between different brain areas is easier to detect because it is better defined spatially (and possibly also, for that reason, of a higher intensity).

Brain Controller

Alternatively or additionally to organizing communication and/or activation of a brain area, in an exemplary embodiment of the invention, the degree of involvement of a brain area in processing is controlled, for example, by selectively activating or depressing that brain area. In an exemplary embodiment of the invention, the activation or inhibition is by electrical field application. Alternatively, the activation or inhibition is by neuronal control from a different brain area.

Thus, the control may be effected by a suitably programmed brain area and/or by an ambulatory device. In an exemplary embodiment of the invention, the brain controller (device/area) recognizes desirable patterns and enhances them and/or detects decline (e.g., lack of operation or over operation of a brain area in a dyslectic user) and counteracts the decline/over-activity. Optionally, the user controls the device, for example, when the user feels that a certain part of his brain is not active enough (e.g., increase in letter misidentification).

Such a controller that includes selective damping and activation may also be used for treating epilepsy, as described above. Possibly, a processor of the controller may be reprogrammed for the different activities.

Non-Brain Applications

While the above description has focused on brain neurons, in an exemplary embodiment of the invention, the neurons, or other cells trained, are outside the brain. For example, the cells can be retinal cells, spinal cells and/or cells in a nervous plexus. Such training may be used to replace and/or supplement unconscious control loops that are programmed into the body, for example, for assisting walking. Alternatively or additionally, the training is used to control glandular secretions, such as from the pancreas, in response to signals from the stomach. Such signals may include signals that go directly from one organ to the other. Alternatively or additionally, the signals include signals that go to the brain and are relayed by the brain between organs.

In an exemplary embodiment of the invention, the controlled organ is the GI tract. It has lately been determined that the slow wave in the intestines is created by a layer of excitable networked tissue in between the two muscular layers. In an exemplary embodiment of the invention, this layer is trained to provide a desired activation pattern of the bowels and/or to respond to commands from an external or implanted device or from the brain. For example, the bowels can be trained to increase or reduce peristalsis speed, to effect correct peristalsis (e.g., to treat irritable bowel syndrome), to stop peristalsis (e.g., after surgery), to evacuate the bowels (in either direction), to relax the bowels (e.g., for examination) and/or to control stomach contractions (e.g., to control hunger and/or assist dieting).

In an exemplary embodiment of the invention, the training comprises stimulating the bowel (or enervating nerves) with electric fields until a desired activity is displayed, and then resting for a duration.

Direct Human Interface and Reflexive Applications

Some of the above applications were described as interfacing between a human and a device. In an exemplary embodiment of the invention, however, the above methods are used to allow a user to interface better with his own brain and/or body.

In an exemplary embodiment of the invention, various workings of the human body, for example, distention of the stomach, and blood glucose level, which are reported by nerves are exposed to conscious parts of the brain. Likewise, sympathetic nerves are connected to conscious parts of the brain. The control may be, for example, using an external device, using direct commands, or by programming (e.g., programming in a diabetes watchdog to monitor high glucose levels).

In an exemplary embodiment of the invention, the exposure of workings is by pairing conscious sensations with the reporting of nerves. One example is pairing glucose level, as sensed by the brain, with a feeling of tingling in the arm. The stronger the tingling, the higher the glucose level.

In another example, control of inner workings is achieved by linking a motor control, e.g., of the arm, to a vagus nerve of the heart, for example to allow conscious control of heart rate.

Alternatively or additionally, the exposure is enhanced by allowing a user to view results and/or inner states using his input sensory modalities, such as vision and/or sound, or by direct activation of memories.

In an exemplary embodiment of the invention, the exposure is used as part of a diagnostic program, in which the user reports the state of his body and/or response to tests. Alternatively or additionally, the exposure is used to aid prevention, for example, by assisting the user in maintaining his health (e.g., food intake, glucose levels). Alternatively or additionally, the exposure and/or control is used for disease cure (e.g., controlling body temperature, blood flow, heart rate, glandular output).

Treatment of Various Disorders by Vagus Nerve Control

It has recently been postulated (e.g., by Cyberonics, Inc. of the USA) that various disease states may be treated by stimulation of vagus nerves. In an exemplary embodiment of the invention, such treatment is provided by inter-neuron stimulation, rather than using implanted electrodes or TMS. For example, control of a vagus nerve may be linked to a motor program or to a large input area, which area is activated by an external device and which motor program is activated under conscious control. Alternatively or additionally, the Cyberonics devices and methods may be used for stimulating the vagus nerve as part of an input signal, as used in the training method above.

For example, the following patents, the disclosures of which are incorporated herein by reference, describe various disease, such as glandular disorders, eating and sleeping disorders, psychiatric disorders and cardiac disorders. In an exemplary embodiment of the invention, the treatments described therein are provided by the brain itself, for example, the brain organizing input and/or output to the vagus nerve, or the brain being taught to directly control or expose the nerve. The patents and publications are:

U.S. Pat. No. 5,928,272 Automatic Activation Of A Neurostimulator Device Using A Detection Algorithm Based On Cardiac Activity U.S. Pat. No. 5,707,400 Treating Refractory Hypertension By Nerve Stimulation U.S. Pat. No. 5,571,150 Treatment Of Patients In Coma By Nerve Stimulation U.S. Pat. No. 5,540,730 Treatment Of Motility Disorders By Nerve Stimulation
U.S. Pat. No. 5,335,657 Therapeutic Treatment Of Sleep Disorder By Nerve Stimulation
U.S. Pat. No. 5,330,515 Treatment Of Pain By Vagal Afferent Stimulation
U.S. Pat. No. 5,299,569 Treatment Of Neuropsychiatric Disorders By Nerve Stimulation
U.S. Pat. No. 5,269,303 Treatment Of Dementia By Nerve Stimulation
U.S. Pat. No. 5,263,480 Treatment Of Eating Disorders By Nerve Stimulation
U.S. Pat. No. 5,231,988 Treatment Of Endocrine Disorders By Nerve Stimulation
U.S. Pat. No. 5,215,086 Therapeutic Treatment Of Migraine Symptoms By Stimulation
WO 93/02744 Treatment Of Anxiety Disorders By Nerve Stimulation
WO 93/01862 Treatment Of Respiratory Disorders By Nerve Stimulation Non-Human Applications Although the above description has focused on human neural networks, the above methods can also be practiced on animals (e.g., mammals such as dogs, cats, mice, rats, bats, dolphins, seals, reptiles such as lizards, fish, amphibians such as frogs, mollusks and/or other invertebrates), inasmuch as null or reduced cooperation is required for some of the methods as compared to standard training methods. In an exemplary embodiment of the invention, the methods are used to train an animal to perform a series of tasks, for example operating test equipment in a spaceship.

In an alternative embodiment of the invention, an animal with a sensitive natural sensor (e.g., sense of smell, profound visual capabilities) is trained and a bio-electrical interface is attached to the animal to receive signals from its sensors. Alternatively, a response to a sensed signal may be programmed into the animal as well. It should be noted that such programmed multi-step and/or logic decision response is very difficult, if not impossible, to achieve for some animals, depending on the level of complexity desired. For example, the programmed logic can includes, for example, two, three, four or more sequential processing steps and/or logic functions (e.g., AND, NAND, XOR). In addition, a look-up table, for example, with 3, 5, 10, 20 or any smaller, intermediate or larger number of entries can be programmed. In some cases, a state machine including 3, 4, 7, 10 or any smaller, intermediate or greater number of states and 1, 2, 3, 5 or any smaller, intermediate or greater number of inputs is programmed into the animal. In another example, a linear, or high order polynomial (e.g., 2, 3, 5 response function is trained into the animal.

In an exemplary embodiment of the invention, the above methods are used to better readout a state of an animal, for example to determine its state of hunger. Alternatively or additionally, the readout is used during standard training, for example, to determine what degree of reward is sufficient to make a desired impression on an animal.

Experimental Data

Figure 11B:
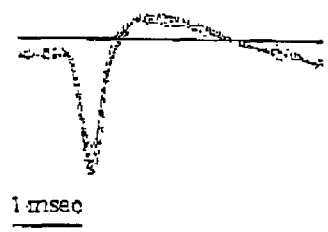

A plurality of learning experiments were performed in cultured networks containing 10,000-50,000 cortical neurons obtained from newborn rats, under the assumption that the organizing principles operating at the level of neuronal populations are intrinsic to neurons, and are therefore manifested ex-vivo. Such cultured cortical networks have been thoroughly studied by others and a substantial amount of data has been accumulated, showing that they are structurally rich, develop and adapt functionally and morphologically over a broad range of time scales, and are experimentally stable over weeks. In order to exploit these advantages, we use the substrate embedded multi-electrode array technology, as shown for example in FIG. 11A. FIG. 11A shows a large random cortical networks cultured on substrate-embedded multi-electrode arrays (A); Scale bar: 30 µm. FIG. 11B shows examples of action potentials recorded from one electrode. The two parallel lines represent ±8 RMS units for this particular electrode.

In what follows we show that the cortical networks display general properties expected from neural systems capable of learning; namely, numerous connections, stability of connections and modifiability by external stimuli. We then describe closed loop experiments in which these biological networks interact with a computer-controlled environment, and demonstrate that the above described training method, in which the elimination of the stimulus acts as a "reward", is sufficient for learning and memorizing arbitrarily chosen tasks defined in terms of neuronal firing patterns.

The cultured neurons form numerous synaptic connections. This is apparent from the large number of statistically significant correlated activities between pairs of electrodes. We operationally define such pairs of neural connectivity in terms of an action potential A that entails another action potential B with a precise time delay ($\tau\pm0.5$ millisecond) between the two.

Figure 11C:
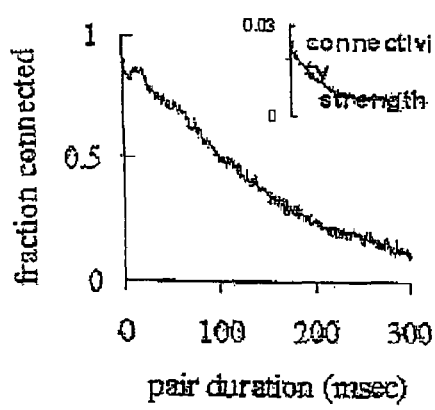

FIG. 11C shows the average number (for four networks) of significantly occurring activity pairs formed between ten randomly chosen active (>0.2 Hz of spontaneous activity) electrodes. This number, normalized to the maximal number of possible activity pairs, is depicted as fraction connected; $\tau$ depicts the within-pair time delay. The inset shows the average functional connectivity strength as a function of $\tau$. (Four different networks; ten randomly chosen active electrodes from each).

FIG. 11C shows that the average number of such statistically significant A→B connections, is a large percentage of the maximum that is possible at relatively small values of $\tau$. As the time delay between the activities of the elements of the pair becomes longer, the realized number of pairs decreases. Of course, a significant occurrence of A→B connection might represent a causal relation between the activity of A and that of B, or a non-causal correlation resulting from co-activation by a common source. Furthermore, many of the observed connections are actually parts of larger groups of significantly connected activities. However, for the purposes of this experiment, distinctions between the possibilities mentioned above are not crucial. Rather, the important thing is that the number of connections is large (FIG. 11C), and that many independent activity patterns exist. The latter is implied from the fact that in these networks single neurons seldom fire spontaneously without being activated by other neurons, while the average correlation between elements of pairs is rather weak (inset of FIG. 11C). The stability of connections in the network may be appreciated by comparing the number of times each of the significantly occurring pairs appeared in ten consecutive time bins (30 minutes each) over five hours of continuous recording. We used the number of times that a given A→B activity pair appeared in the first 30 minutes bin, divided by the number of occurrences of A OR B as a measure for the pair's occurrence probability. Using the binomial theorem we identified pairs whose count did not change in a statistically significant manner in subsequent time bins.

Figure 11D:
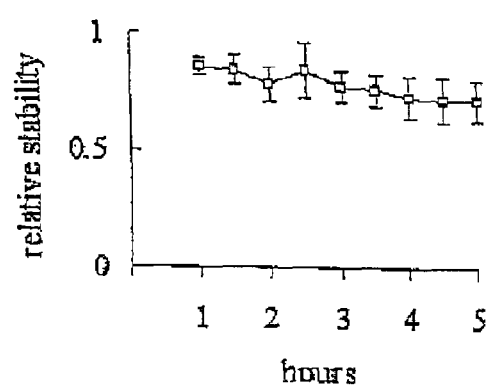

FIG. 11D shows the stability of neural activity pairs over hours. Ten active (>0.2 Hz of spontaneous activity) electrodes were chosen randomly. All the occurrences of pairs ($\tau$=50 milliseconds) are counted in ten half-hour bins. For each such time bin, the corresponding point in the graph shows the fraction of pairs that their count did not change in a statistically significant manner (p<0.01), relative to their count in the first half-hour. Data was averaged over four networks, and standard deviation bars were added.

FIG. 11D shows that approximately 70% of the pairs remained unchanged after five hours of spontaneous activity.

When stimulating currents are delivered through a pair of substrate embedded electrodes at a constant frequency, the network responds by generating a rich repertoire of reverberating electrical activities, lasting 100 milliseconds or more.

Figure 12A:
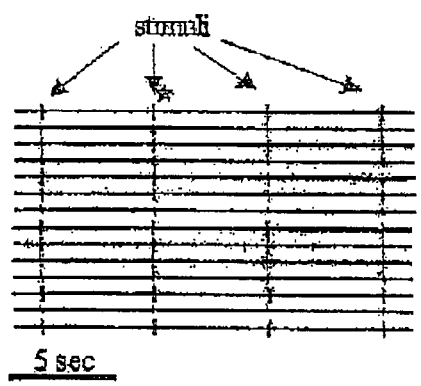
FIGS. 12A-12B show network response to focal stimulation, in a network of the type of FIG. 11.
Figure 12B:
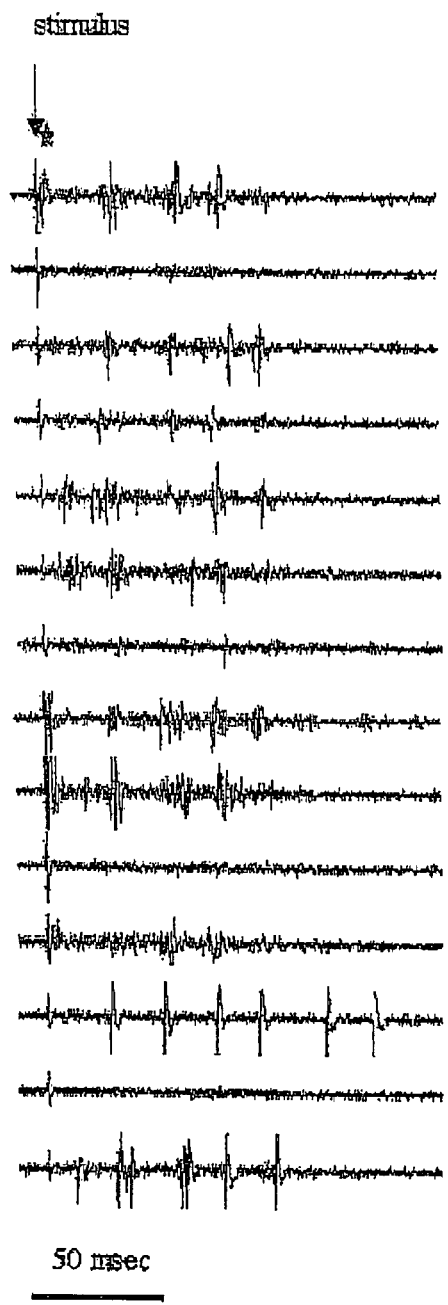

FIG. 12A and FIG. 12B show network response to focal stimulation. A stimulus pulse lasts 420 μSec, and its amplitude is 50 μA. The traces were recorded simultaneously from different electrodes.

Figure 12C:
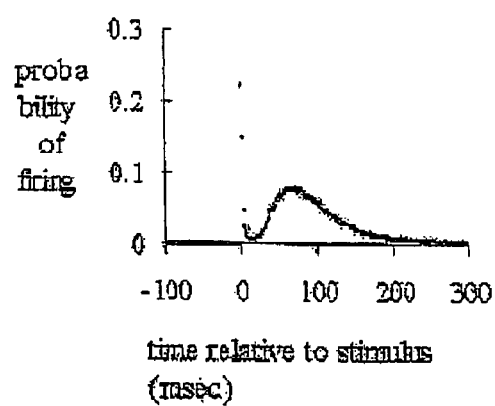
FIG. 12C shows a Peri-stimulus time histogram (PSTH)

FIG. 12C shows a Peri-stimulus time histogram (PSTH). The first peak represents direct activation of neurons by the stimulus; the second peak represents a reverberating response.

Modifications in functional connectivity would be manifested as changes in the coupling of such responses to the stimulus. Indeed, repeated stimulation induces changes in network responsiveness as previously shown by others. Moreover, the direction and the magnitude of such modifications change with time, reflecting the myriad activation pathways and activity-dependent mechanisms that operate in these networks.

Figure 12D:
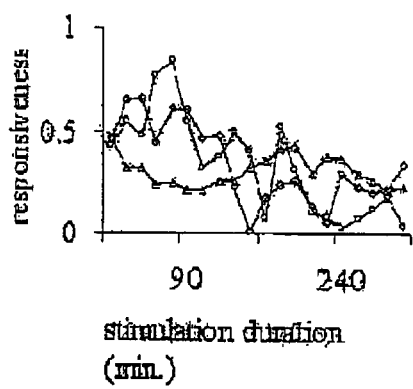
FIG. 12D shows the responsiveness of three electrodes (from three different networks) to a long lasting series of stimulation at ⅓ Hz recorded from three different networks.

FIG. 12D shows the responsiveness of three electrodes (from three different networks) to a long lasting series of stimulation at ⅓ Hz recorded from three different networks. Responsiveness is here defined as the average number of threshold crossing spikes within 50±10 milliseconds following one stimulus; responsiveness is calculated in bins of 10 minutes each (i.e. from responses to 200 stimuli). FIG. 12D, as well as the data that will be presented in what follows demonstrate this "exploratory" nature of the change in response to series of stimuli.

The analyses presented above imply that cortical networks display general properties expected from neural systems capable of learning; namely, numerous connections, stability of connections and modifiability by external stimuli. We now turn to the experiments that demonstrate learning in a cortical network without the involvement of a neural rewarding entity, for example using the method described above.

Each experiment is started by stimulating the network through a pair of electrodes and observing the responsiveness of all other (i.e. the non-stimulated) electrodes. An electrode that responds 50 (±10) milliseconds after a stimulus with a response to stimulus (R/S) ratio of 1/10 or less is selected. In other words, before training, it takes at least 10 stimuli in order to evoke one action potential in the selected electrode within the designated time frame of 50 (±10) milliseconds after a stimulus. During the training phase, the learning task is to selectively increase the R/S of the selected electrode to 2/10 or greater at the designated time window of 50 (±10) milliseconds after a stimulus. The network is continuously stimulated at a constant frequency of ⅓, ½ or 1 stimuli per second. A computer constantly monitors the R/S of the selected electrode, and once the criterion of R/S≧2/10 is fulfilled, the computer automatically stops the stimulation. After five minutes, the network is stimulated again (at the same low frequency) until the criterion R/S≧2/10 in the same selected electrode is fulfilled again. This stimulation cycle, which is composed of five minutes without stimulation followed by low-frequency (⅓, ½, or 1 Hz) stimulation until R/S≧2/10 criterion in the selected electrode is fulfilled, is repeated several times. As a rule, if the criterion is not fulfilled within ten minutes of stimulation, the stimulation is stopped for five minutes. Hence, the maximal duration of one stimulation cycle is 15 minutes (i.e. 10 minutes of stimulation and 5 minutes of quiescence). The latency for reaching the predetermined criterion (referred to as response time) in each stimulation cycle is used as a measure for the strength of S-R connection, and may be viewed as a measure of the degree to which the task was learned, in the experimental setting.

Figure 13A:
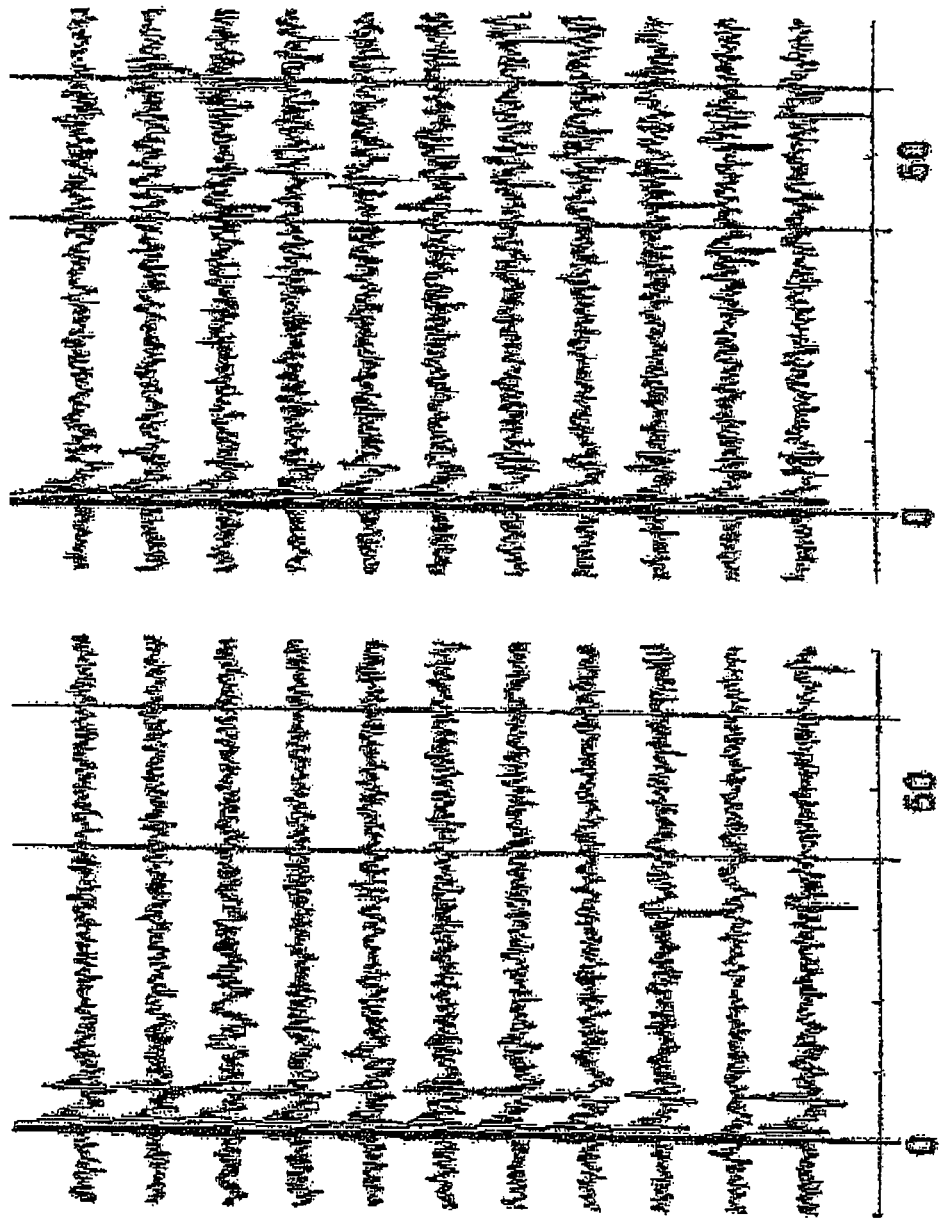
FIG. 13A shows an example of learning in a cultured network of cortical neurons.

FIG. 13A shows an example of learning in a cultured network of cortical neurons. Each trace within a panel shows recordings obtained 10 msec before the stimulus to 70 msec after the stimulus, before (left) and after (right) the training procedure. This figure includes the responses of a selected electrode before (left column) and after (right column) training. The eleven traces of each panel show the responses to eleven consecutive stimulation pulses. Note that the activity within the 50 (±10) milliseconds window (depicted) is markedly increased after the training phase. In order to enhance selectivity of the R/S increase in the selected electrode, we concomitantly monitor a second electrode in the array, which serves as a measure for global network responsiveness. The stimulus is removed only if the fulfillment of the R/S criterion in the selected electrode is not accompanied by similar increase in the responsiveness of the second electrode. Selectivity is demonstrated in FIG. 13B.

FIG. 13B shows records from three electrodes. Each trace within a panel shows recordings obtained 100 msec before the stimulus to 100 msec after the stimulus. The top two panels show the response of the electrode that was selected for learning. Note that the responsiveness of the selected electrode, but not the control electrodes (shown in the other panels), increased appreciably. This figure includes the responses of a selected electrode (top panels), and two other electrodes, before (left column) and after (right column) training. Again, the activity within the 50 (±10) milliseconds window (depicted) is markedly increased after the training phase. This increase does not represent a global increase in the responsiveness of the network, as implied by the lack of appreciated change in the responsiveness of the two control electrodes that are shown in the figure. The control electrodes were chosen by analyzing the data, after the completion of the experiment, based on their similarity to the responsiveness of the selected electrode before the training.

Figure 14A:
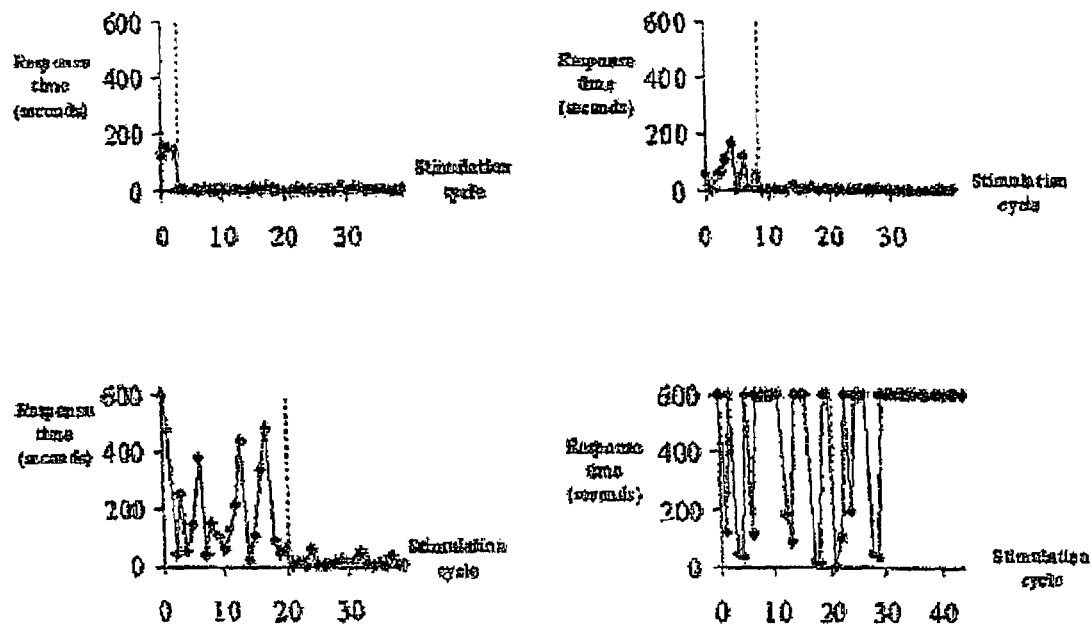
FIG. 14A shows four learning curves, differing in their learning kinetics.

FIG. 14A shows three learning curves (top row panels and bottom left panel), differing in the learning kinetics. In these curves, the response time (i.e. time required for the selected electrode to fulfill the R/S≧2/10 criterion) is plotted against the number of stimulation cycle. (Recall that each stimulation cycle is composed of five minutes without stimulation followed by low-frequency stimulation until R/S≧2/10 criterion is fulfilled.) FIG. 14A (the three curves) shows that the time required to instruct a network to perform the task varies, reflecting the arbitrariness of the procedure by which the tasks are chosen and the idiosyncrasies of the networks. This variability faithfully represents the spectrum of learning curves observed in our networks (n>30 from 16 different networks).

Figure 14B:
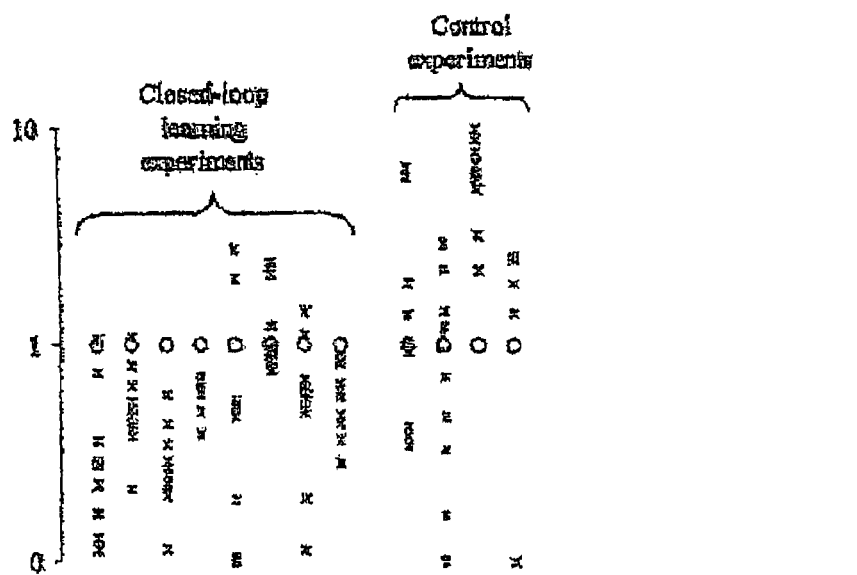
FIG. 14B (left eight columns) shows that the learning achieved under these conditions can be selective.

FIG. 14B (left eight columns) shows that the learning achieved under these conditions can be selective. Changes in R/S of the selected electrodes (open circles) and ten control electrodes (stars) are depicted for eight experiments from eight different networks. For each network, the ten control electrodes were chosen by analyzing the data, after the completion of the experiment, based on their similarity to the R/S of the selected electrode before the training. The point in time that separates the period before training and that of after training is depicted by a broken line. The change, depicted by f, is defined as the ratio between the responsiveness before training, and responsiveness after training, normalized to the change in R/S of the selected electrode. Thus, f=1 means a change in R/S that is identical to the change measured in the selected electrode. f>1 and f<1 mean that the relevant response of a control electrode increased or decrease, respectively, relative to the selected electrode. Note that the strengthening in the response to stimulus ratio (R/S) of the selected electrode is generally higher relative to the responsiveness change in the control electrodes. Also note that since the selected and control electrodes demonstrate fairly low responsiveness before the training, a bias towards an average increase of R/S during training is introduced. The reported effect is selective inasmuch as the increase in R/S of the selected electrode is more than the average increase for the control electrodes. The probability of the selected electrode to be ranked $4^{th}$ or higher (out of 11), as is the case in the eight experiments shown, is $O(4/11)^8$. While learning can be achieved in practically every experiment, selective learning such as that appearing in FIG. 14B is more difficult to achieve. Only about half of our attempts were successful within 25 stimulation cycles.

The notion that "driving" stimulus removal is necessary for selecting "appropriate" network responses is further supported by the experiment shown bottom right panel of FIG. 14A. In this experiment the fulfillment of the R/S criterion in the selected electrode did not lead to stimulus removal (i.e. the attainment of the criterion was ignored). The stimulation was delivered for 10 minutes interrupted by 5 minutes of quiescence, regardless of the responses recorded from the selected electrode. The response time (i.e. the time required for first appearance of R/S≧2/10 within each stimulation cycle), is plotted against the stimulation cycle number, and shows large fluctuations. FIG. 14B (right four columns) shows the change in R/S of the selected and control electrodes in four such experiments. Without exception, learning does not occur if the "appropriate" response does not remove the stimulus.

Methods of the Experiments

Culture techniques. Cortical neurons are obtained from newborn rats within 24 hours from birth, following standard procedures. The cortex tissue is digested enzymatically and mechanically dissociated. The neurons are plated directly onto substrate-integrated multi-electrode array (MEA) dishes (see below). The cultures are bathed in MEM supplemented with heat-inactivated horse serum (5%), Glutamine (0.5 mM), Glucose (20 mM), and Gentamycin (10 µg/ml), and maintained in an atmosphere of 37° C., 5% $CO_2$ and 95% air in a tissue culture incubator and during the recording phases. Half of the medium is exchanged twice a week. Experiments are performed in the third week after plating, thus allowing complete maturation of the neurons. Networks that did not respond (in the third week after plating) to repeated low frequency stimulation (1, ½, ⅓ Hz) were not kept for further experimentation.

The electrical activity of the cultured network is dependent upon synaptic transmission: there are many published reports showing that the electrical activity in a cultured cortical network may be blocked by perfusion with the N-Methyl-D-aspartate (NMDA) receptor antagonist D-2-amino-5-phosphonovalerate (APV) and non-NMDA receptor antagonist 6-cyano-7-nitroquinoxaline-2,3-dion (CNQX). We repeated these experiments, using intracellular recordings as well as MEA recordings. We find that in the presence of 5 µM bicuculin, 10 µM DNQX and 20 µM APV, spiking activity within the cultured network is completely abolished.

Electrophysiological methods. We use arrays of 60 Ti/Au/TiN electrodes, 30 µm in diameter, spaced 200 µm from each other (MultiChannelSystems (MCS), Reutlingen, Germany). The insulation layer (silicon nitride), is pretreated with poly-L-lysine forming a good surface for network development. A commercial 60-channel amplifier (B-MEA-1060, MCS, Reutlingen, Germany) with frequency limits of 10-3000 Hz and a gain of ×1024 is used. The B-MEA-1060 is connected to MCPPlus filter amplifiers (Alpha Omega, Nazareth, Israel) for further amplification (×10 to ×20). Stimulation through the MEA is performed using a dedicated 8-channel stimulus generator (MCS, Reutlingen, Germany). Micro-incubation environment is arranged, to support long-term recordings from MEA dishes. This is achieved by streaming a filtered, heated and humidified air/$CO_2$ (95/5%) gas mixture, and by electrically heating the MEA platform to 37° C. Data is digitized using two 5200a/526 A/D boards (Microstar Laboratories, WA, USA).

Analysis. Each channel is sampled at a frequency of 24 Ksample/second and prepared for analysis using the Alpha-Map interface (Alpha Omega, Nazareth, Israel).

Spike detection: Thresholds (×8 Root Mean Square (RMS) units; typically in the range of 10-20 µVolt) are separately defined for each of the recording channels prior to the beginning of the experiment. No further spike sorting techniques are applied. We defined elementary activities on the basis of their participation in statistically significant activity pairs as explained below, where every threshold crossing is considered in the analysis. The major limitation of this approach is that it takes more occurrences of a particular pair in order to define statistical significance. This limitation was overcome by performing long experiments.

Definition of activity pairs: We operationally define pairs of neural connectivity in terms of an action potential A that entails another action potential B with a precise time delay (τ±0.5) millisecond between the two. A and B may be action potentials recorded in the same or in different measuring electrodes. Both events (A and B) are defined by threshold crossing as explained above. The number of measuring electrodes ($N_e$) dictates the maximal number of detectable pairs. Thus for a τ>0, the maximal number of A→B pairs is $N_e^2$. For τ=0, the maximal number of A→B pairs is $N_e(N_e-1)$; (an activity cannot pair with itself within a zero time delay).

$$p(k) = \sum_{i=k}^{\infty} \binom{n}{i} p_B^i (1-P_B)^{n-i} = 1 - \sum_{j}^{k-1} \binom{n}{j} p_B^j (1-P_B)^{n-j}$$

Statistical significance of activity pairs: The statistical significance (p-value) of a given A→B pair is calculated under binomial distribution assumptions given the number of times A occurred, the number of time A→B occurred with a time delay τ, and the probability of event B. Thus, if p(k) is the probability of observing k or more A→B pairs out of n A events, and $P_B$ is the probability of a B event, then p-value<0.01 was used as a significance measure.

Functional strength of a pair (data of FIG. 11C, inset): Given an A→B activity pair, the forecasting of B by A, which is the strength of the functional connectivity between the two, is given in terms of a correlation coefficient, calculated from the number of times that the given pair appears within 1 hour, divided by the number of occurrences of A OR B.

Stability of activity pairs (data of FIG. 11D): For each A→B pair, statistical significance of a change in pair co-occurrence counts was calculated under the assumptions of the binomial distribution (see above). For instance, suppose that A→B pair (with, e.g., τ=20 milliseconds) appeared $n_1$ times in the first half-hour bin, and $n_4$ times in the fourth half-hour bin. To state that $n_4$ is significantly different from $n_1$, we calculate the probability of finding $n_4$, using the frequency of A→B (at τ=20 milliseconds) in the first half-hour bin as the theoretical probability, and the number of A events in the fourth half-hour bin as the number of trials. If the calculated probability is <0.01, n4 is significantly different from n1.

PSTH construction (data of FIG. 12C): A series of 1200 stimuli (420 μSec, 50 μA, ⅓ Hz) is delivered through a pair of electrodes, and the responses in 10 randomly chosen active electrodes are recorded. The total number of responses (counted in 1 millisecond time bins) divided by 12000 is presented, time-locked to the stimulus event. Thus the probability of firing as a function of time is obtained.

It will be appreciated that the above-described methods of training may be varied in many ways, for example, changing the order of steps in training or the number of training iterations. While the application has focused on training the brain, other neural networks are intended as well. In addition, while the description has focused at times on single neurons, the application includes stimulating, reading and training of groups of neurons as well. In addition, a multiplicity of various features, both of methods and of devices has been described. Where methods are described, devices for carrying out the methods are also contemplated. It should be appreciated that different features may be combined in different ways. In particular, not all the features shown above in a particular embodiment are necessary in every similar exemplary embodiment of the invention. Further, combinations of the above features are also considered to be within the scope of some exemplary embodiments of the invention. Also within the scope of the invention are devices and/or software for programming existing devices to make the device comply with the methods described herein. Section headings where they appear are meant for clarity of browsing only and should not be construed as limiting the contents of a section to that particular section. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

The invention claimed is:

1. A method of training an in-vivo biological neural network in a living human using a controller, comprising:
applying a cycle comprising:
stimulating a neural network by said controller applying at least an input signal to the network;
detecting an output response of the network by said controller; and
modifying said stimulation by said controller for at least a period of time if said response matches a desired at least approximate response; and
repeating said cycle of stimulation, detection and modification at least one more time until said neural network is trained to generate a desired output response for said input signal.

2. A method according to claim 1, wherein said input signal is a specific signal and wherein stimulating comprises applying a less specific stimulation.

3. A method according to claim 1, wherein said modifying comprises modifying said input signal.

4. A method according to claim 1, wherein said modifying comprises stopping said stimulation.

5. A method according to claim 1, wherein said modifying is applied in a manner known to affect a stability of connections in said network.

6. A method according to claim 1, wherein said modifying is applied in a manner known to affect a learning behavior of said neurons of said network.

7. A method according to claim 1, wherein said stimulating comprises stimulating using a magnetic field stimulator.

8. A method according to claim 1, wherein said stimulating comprises stimulating using an electric current.

9. A method according to claim 1, wherein said modifying comprises applying a chemical agent.

10. A method according to claim 1, wherein said modifying comprises applying an electric field.

11. A method according to claim 1, comprising modifying said method by said controller in response to a response of said network to said method.

12. A method according to claim 1, wherein said desired output response is a particular defined response.

13. A method according to claim 1, wherein said desired output response is a random response pattern indicative of an unlearning by said network.

14. A method according to claim 1, wherein said desired output response is a spatial shift in a portion of said network that responses to said input, from a previous responding portion to a shifted responding portion.

15. A method according to claim 1, comprising changing said input pattern during a repetition cycle.

16. A method according to claim 1, comprising increasing a resolution of said input pattern between repetition cycles.

17. A method according to claim 1, comprising requiring an output response with a reduced range of acceptable values in subsequent repetition cycles.

18. A method according to claim 1, wherein repeating comprises repeating until an area of said network is organized to act as an input interface for said network for direct setting of network values not via a network's standard inputs.

19. A method according to claim 1, wherein repeating comprises repeating until an area of said network is organized to act as an output interface for said network for direct receiving of network values not via a network's standard outputs.

20. A method according to claim 1, comprising:
providing a complex output response pattern to inputs to be trained into said network;
dividing said response pattern into sub-patterns;
training said sub-patterns individually; and
linking said sub-patterns.

21. A method according to claim 1, comprising training a desired output response pattern to inputs as a whole into said network.

22. A method according to claim 1, wherein said network is a GI motor complex.

23. A method according to claim 1, wherein said network is a nervous plexus.

24. A method according to claim 1, wherein said network is comprised in a brain.

25. A method according to claim 24, wherein said controller replaces at least one natural learning related function of said brain.

26. A method according to claim 24, wherein said output is measured on said brain.

27. A method according to claim 24, wherein said output is measured as a response of said human.

28. A method according to claim 24, wherein said input is provided directly to said brain.

29. A method according to claim 24, wherein said stimulation is provided directly to said brain.

30. A method according to claim 24, wherein said stimulation is provided to said brain via natural senses.

31. A method according to claim 24, wherein said input is provided to said brain via natural senses.

32. A method according to claim 24, wherein modifying said stimulation comprising controlling the propagation of a signal inside said brain.

33. A method according to claim 24, wherein said method is used to rehabilitate an old function of said network.

34. A method according to claim 24, wherein said method is used to teach a new function to said network.

35. A method according to claim 24, wherein said method is used to teach new motor programs to said network.

36. A method according to claim 24, wherein said method is used to create a new pathway in said brain.

37. A method according to claim 24, wherein said method is used to create a new function area in said brain.

38. A method according to claim 24, wherein said method is used to remap a function from one brain area to another in said brain.

39. A method according to claim 24, wherein said method is used to erase a learned pattern from said brain.

40. A method according to claim 24, wherein said method is used to create a digital logic functioning area in said brain.

41. A method according to claim 24, wherein said method is used to train the brain in the use of an artificial organ.

42. A method according to claim 41, wherein said organ is a replacement organ.

43. A method according to claim 41, wherein said organ is a new organ not corresponding to a previous organ controlled by said brain.

44. A method according to claim 24, wherein said human is not conscious during the application of said method.

45. A method according to claim 24, wherein said human is not in control of learning processes imposed by said method.

46. A method according to claim 24, comprising not motivating said human in response to the output.

47. A method according to claim 24, wherein said human reports said output.

48. A method according to claim 24, wherein said human generates said input.

49. A method according to claim 24, comprising performing actions by said human to capture previously trained un-associated input-output response patterns.

50. A method according to claim 24, wherein said input is an input internal to said brain.

51. A method according to claim 24, wherein said output is an output internal to said brain.

52. A method according to claim 24, wherein said output comprises controlling an epilepsy attack.

53. A method according to claim 24, wherein said output comprises reducing a sensation of pain.

54. A method of training a biological neural network using a controller, comprising:
   applying a cycle comprising:
      stimulating a neural network by said controller applying at least an input signal, which is a localized signal, to the network, wherein said stimulating comprises applying a less localized stimulation;
      detecting an output response of the network by said controller, and
      modifying said stimulation by said controller for at least a period of time if said response matches a desired at least approximate response; and
   repeating said cycle of stimulation, detection and modification at least one more time until said neural network is trained to generate a desired output response for said input signal.

55. A method according to claim 54, wherein said modifying comprises reducing said less localized stimulation.

56. A method according to claim 54, wherein said modifying comprises increasing said less localized stimulation.

57. A method according to claim 54, wherein said network is an in-vivo network in a living non-human animal.

58. A method according to claim 57, comprising:
   providing a potential environmental contaminant;
   repeating said method under at least two conditions of said contaminant; and
   comparing a response of said network to said method to determine an effect of said contaminant on training of said animal.

59. A method according to claim 57, comprising:
   selecting a network portion of said animal that is coupled to a sensing ability of said animal; and
   training said network portion to output at least an indication of a sensing by said animal.

60. A method according to claim 57, wherein said input is a command that can be sensed by said animal and wherein said desired output is a behavioral response of said animal.

61. A method according to claim 60, wherein said input and said output are inter-related using a complex logic, including at least two logic steps.

62. An animal trained according to the method of claim 57.

63. A method of training an in vitro biological neural network using a controller, comprising:
   applying a cycle comprising:
      stimulating a neural network by said controller applying at least an input signal to the network;
      detecting an output response of the network by said controller; and
      modifying said stimulation by said controller for at least a period of time if said response matches a desired at least approximate response; and
   repeating said cycle of stimulation, detection and modification at least one more time until said neural network is trained to generate a desired output response for said input signal.

64. A method according to claim 63, wherein said network is grown in a container.

65. A method according to claim 63, wherein said network is excised from a living body to a container.

66. A method according to claim 63, comprising:
   providing a potential environmental contaminant;
   repeating said method under at least two conditions of said contaminant; and
   comparing a response of said network to said method to determine an effect of said contaminant on training of said network.

* * * * *